(12) United States Patent
Casci et al.

(10) Patent No.: US 10,040,690 B2
(45) Date of Patent: Aug. 7, 2018

(54) STA-18, A NEW MEMBER OF THE SFW FAMILY OF MOLECULAR SIEVE ZEOTYPES, METHODS OF PREPARATION AND USE

(71) Applicant: Johnson Matthey Public Limited Company, London (GB)

(72) Inventors: John Casci, Billingham (GB); Alessandro Turrina, Billingham (GB); Raquel Garcia Salas, Billingham (GB); Paul Wright, St. Andrews (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 15/493,371

(22) Filed: Apr. 21, 2017

(65) Prior Publication Data

US 2017/0305751 A1  Oct. 26, 2017

Related U.S. Application Data

(60) Provisional application No. 62/326,194, filed on Apr. 22, 2016.

(51) Int. Cl.

| C01B 39/54 | (2006.01) |
| B01J 29/82 | (2006.01) |
| C01B 39/04 | (2006.01) |
| C07C 211/08 | (2006.01) |
| C07D 471/08 | (2006.01) |
| C09C 1/34 | (2006.01) |
| G01N 23/20 | (2018.01) |
| H01J 37/28 | (2006.01) |
| B01J 29/84 | (2006.01) |
| B01J 29/85 | (2006.01) |
| B01J 29/83 | (2006.01) |
| C01B 39/48 | (2006.01) |

(52) U.S. Cl.
CPC ............ *C01B 39/04* (2013.01); *B01J 29/82* (2013.01); *B01J 29/83* (2013.01); *B01J 29/84* (2013.01); *B01J 29/85* (2013.01); *C01B 39/54* (2013.01); *C07C 211/08* (2013.01); *C07D 471/08* (2013.01); *C09C 1/343* (2013.01); *G01N 23/20* (2013.01); *H01J 37/28* (2013.01); *C01B 39/48* (2013.01)

(58) Field of Classification Search
CPC .......... C01B 39/04; C01B 39/54; B01J 29/82; B01J 29/83; B01J 29/84; B01J 29/85
See application file for complete search history.

(56) References Cited

U.S. PATENT DOCUMENTS

| RE34,804 E | 12/1994 | Lachman et al. |
| 5,492,883 A | 2/1996 | Wu |
| 5,565,394 A | 10/1996 | Lachman et al. |
| 5,633,217 A | 5/1997 | Lynn |
| 5,656,244 A | 8/1997 | Cole |
| 2015/0246345 A1 | 9/2015 | Collier et al. |
| 2015/0246346 A1* | 9/2015 | Chandler ............... B01J 29/072 502/74 |
| 2016/0068402 A1* | 3/2016 | Liu .......................... C01B 39/06 423/703 |
| 2017/0305751 A1* | 10/2017 | Casci ...................... C01B 39/04 |

FOREIGN PATENT DOCUMENTS

| WO | 200109037 A1 | 2/2001 |
| WO | 2016039825 A1 | 3/2016 |

OTHER PUBLICATIONS

Turrina et al, "Retrosyntheitic Co-Templating Method for the Preparation of Silicoaluminophosphate Molecular Sieves", Chemistry of Materials, (Jun. 17, 2016) 28, 4998-5012.*

Noble et al.; The templated synthesis and structure determination by synchrotron microcrystal diffraction of the novel small pore magnesium aluminophosphate STA-2†; J. Chem. Soc., Dalton Trans., 1997, pp. 4485-4490.

Xie et al.; SSZ-52, a Zeolite with an 18-Layer Aluminosilicate Framework Structure Related to That of the DeNOx Catalyst Cu-SSZ-13; dx.doi.org/10.1021/ja4043615 | J. Am. Chem. Soc. 2013, 135, 10519-10524.

Davis et al.; Computationally Guided Synthesis of SSZ-52: A Zeolite for Engine Exhaust Clean-up; Chem. Mater. 2016, 28, 708-711.

* cited by examiner

*Primary Examiner* — David M Brunsman

(57) ABSTRACT

STA-18, a molecular sieve having a SFW structure and containing phosphorus in the framework, is described. STA-18AP (as prepared) can have a lower alkyl amine, such as trimethylamine, and one of 1,6-(1,4-diazabicyclo[2.2.2]octane)hexyl cations (from diDABCO-C6) or 1,7-(1,4-diazabicyclo[2.2.2]octane)heptyl cations (from diDABCO-C7) or 1,8-(1,4-diazabicyclo[2.2.2]octane)octyl cations (from diDABCO-C8) as SDAs. A lower alkyl ammonium hydroxide, such as tetrabutylammonium hydroxide, can be used as a pH modifier for making SAPO STA-18. A calcined product, STA-18C, formed from STA-18AP is also described. Methods of preparing STA-18AP, STA-18C and metal containing calcined counterparts of STA-18C are described along with methods of using STA-18C and metal containing calcined counterparts of STA-18C in a variety of processes, such as treating exhaust gases and converting methanol to olefins are described.

22 Claims, 5 Drawing Sheets

STA-18, A NEW MEMBER OF THE SFW FAMILY OF MOLECULAR SIEVE ZEOTYPES, METHODS OF PREPARATION AND USE

CROSS-REFERENCE TO RELATED APPLICATIONS

This application claims priority to U.S. Provisional Application No. 62/326,194, filed on Apr. 22, 2016, which is incorporated herein by reference.

FIELD OF INVENTION

The present invention relates to STA-18, a new member of the SFW family of molecular sieve zeotypes containing phosphate within the framework. As made SAPO STA-18 (STA-18AP) was produced using trimethylamine and one of 1,6-(1,4-diazabicyclo[2.2.2] octane)hexyl dibromide (diD-ABCO-C6) or 1,7-(1,4-diazabicyclo[2.2.2]octane)heptyl dibromide (diDABCO-C7) or 1,8-(1,4-diazabicyclo[2.2.2] octane)octyl dibromide (diDABCO-C8) as structure directing agents (SDAs). A calcined product (STA-18C) was formed from as-produced SAPO STA-18AP. The invention also relates to methods of preparation of STA-18AP and STA-18C and methods using STA-18C as a catalyst.

BACKGROUND OF THE INVENTION

Molecular sieve zeotypes are a commercially important class of materials that have distinct crystal structures with defined pore structures that are shown by distinct X-ray diffraction (XRD) patterns and have specific chemical compositions. The crystal structure defines cavities and pores that are characteristic of the specific type of molecular sieve zeotype.

Molecular sieves have numerous industrial applications, and zeolites of certain frameworks, such as CHA, are known to be effective catalysts for treating combustion exhaust gas in industrial applications including internal combustion engines, gas turbines, coal-fired power plants, and the like. In one example, nitrogen oxides ($NO_x$) in the exhaust gas can be controlled through a so-called selective catalytic reduction (SCR) process whereby $NO_x$ compounds in the exhaust gas are contacted with a reducing agent in the presence of a zeolite catalyst.

Two types of molecular sieve zeotypes are aluminosilicate zeolites and silicoaluminophosphates (SAPOs). Zeolites were traditional considered to be crystalline or quasi-crystalline aluminosilicates constructed of repeating $TO_4$ tetrahedral units with T being most commonly Si and Al (although other T-atoms and combinations of T-atoms are known). These units are linked together to form frameworks having regular intra-crystalline cavities and/or channels of molecular dimensions. Aluminosilicate zeolites can also be distinguished on the basis of their chemical composition such that zeolites X and Y are both FAU topological types but have different silica-alumina ratios (different SARs). Similarly, SSZ-13 has the CHA topological type but has a higher SAR than previous CHA topological types. Such differences in chemical composition reflect profound differences in both the preparative conditions and the properties and applications of the resulting material.

SAPO's have a three-dimensional microporous crystalline framework made of $PO_2^+$, $AlO_2^-$, and $SiO_2$ tetrahedral units. Because an aluminophosphate ($AlPO_4$) framework is inherently neutral, the incorporation of silicon into the $AlPO_4$ framework by substitution generates a charge imbalance and this can lead to these materials having acidity. Controlling the quantity and location of silicon atoms incorporated into an $AlPO_4$ framework is important in determining the catalytic properties of a particular SAPO molecular sieve, such that as with aluminosilicate zeolites the precise chemical composition of the framework is important in defining the properties and applications.

Numerous types of synthetic zeolites have been synthesized and each has a unique framework based on the specific arrangement its tetrahedral units. By convention, each topological type is assigned a unique three-letter code (e.g., "GME") by the International Zeolite Association (IZA).

The catalytic properties of both aluminosilicate zeolites and SAPO materials can be modified after the aluminosilicate zeolite and/or SAPO molecular sieve has been synthesized. This type of "post-synthesis" modification can be accomplished by treating the (usually calcined form) of the molecular sieve with metallic, semi-metallic or non-metallic materials comprising nickel, cobalt, manganese, magnesium, barium, strontium, lanthanides, actinides, fluorine, chlorine, chelating agents, and others. The modifiers may or may not become part of the final composition of the modified catalyst.

Synthetic zeolites of the SFW topological type when prepared as aluminosilicate compositions are produced using structure directing agents (SDAs), also referred to as a "templates" or "templating agents". The SDAs that are used in the preparation of aluminosilicate SFW topological type materials are typically complex organic molecules which guide or direct the molecular shape and pattern of the zeolite's framework. Generally, the SDA can be considered as a mold around which the zeolite crystals form. After the crystals are formed, the SDA can be removed from the interior structure of the crystals, leaving a molecularly porous aluminosilicate cage.

In typical synthesis techniques, solid zeolite crystals precipitate from a reaction mixture which contains the framework reactants (e.g., a source of silica and a source of alumina), a source of hydroxide ions (e.g., NaOH), and an SDA. Such synthesis techniques usually take several days (depending on factors such as crystallization temperature) to achieve the desired crystallization. When crystallization is complete, the solid precipitate containing the zeolite crystals can be separated from the mother liquor which can be discarded. This discarded mother liquor contains unused SDA, which is often degraded due to harsh reaction conditions, and unreacted silica.

The SFW framework has been recently discovered and synthesised as an aluminosilicate (SSZ-52) by Zou and coworkers (D. Xie, L. B. McCusker, C. Baerlocher, S. I. Zones, W. Wan, X. Zou, *J. Am. Chem. Soc.*, 2013, 135, 10519-10524) The use of a polycyclic quaternary ammonium cation (N,N-diethyl-5,8-dimethyl-2-azonium bicyclo [3.2.2]nonane) as SDA leads to the formation of a stacking-faulted structure. More recently, alternative SDAs (N-ethyl-N(2,4,4-trimethylcyclopentyl)pyrrolidinium or N-ethyl-N-(3,3,5-trimethylcyclohexyl)pyrrolidinium) have been designed and used to prepare SSZ-52. However, the reported PXRD patterns indicate considerable faulting (T. M. Davis, A. T. Liu, C. M. Lew, D. Xie, A. I. Benin, S. Elomari, S. I. Zones, M. W. Deem, Chem. Mater., 2016, 28(3), 708-711).

There is a need to develop new molecular sieves having the basic structure of known molecular sieves, where minor changes in the structure can affect one or more of the catalytic properties of the molecular sieve. In some cases, while minor changes in the structure may not be discernable using normally used analytical techniques, the catalytic activity of the structurally modified molecular sieves may be improved relative to very closely related analogous molecular sieves. Unexpected improvements in the catalytic activity of such structurally modified molecular sieves can allow for the compositions of exhaust gases from engines to meet various regulatory requirements.

SUMMARY OF THE INVENTION

In a first aspect of the invention, provided is a calcined molecular sieve, STA-18C, comprising an SFW type framework having phosphate within the framework. STA-18C can be made by calcining STA-18AP (as-prepared) that contains structure directing agents. The structure directing agents are preferably a 1,4-diazabicyclo [2.2.2]octane derivative (SDA1) and a lower alkyl amine (SDA2). A lower alkyl ammonium hydroxide, tetrabutylammonium hydroxide (TBAOH), was used as a pH modifier in the preparation of SAPO STA-18.

In a second aspect of the invention, provided is a method of preparing the molecular sieve of the first aspect of the invention.

In a third aspect of the invention, provided is composition prepared for manufacturing a molecular sieve having an STA-18 framework of the first aspect of the invention.

In a fourth aspect of the invention, provided is catalytic composition comprising a molecular sieve of the first aspect of the invention.

In a fifth aspect of the invention, provided is a method for treating an exhaust gas from an engine by contacting the exhaust gas with STA-18C or a metal impregnated STA-18C.

In a sixth aspect of the invention, provided is a method of converting methanol to an olefin (MTO) by contacting methanol with STA-18C or a metal impregnated STA-18C.

DETAILED DESCRIPTION OF THE INVENTION

Figure 1:
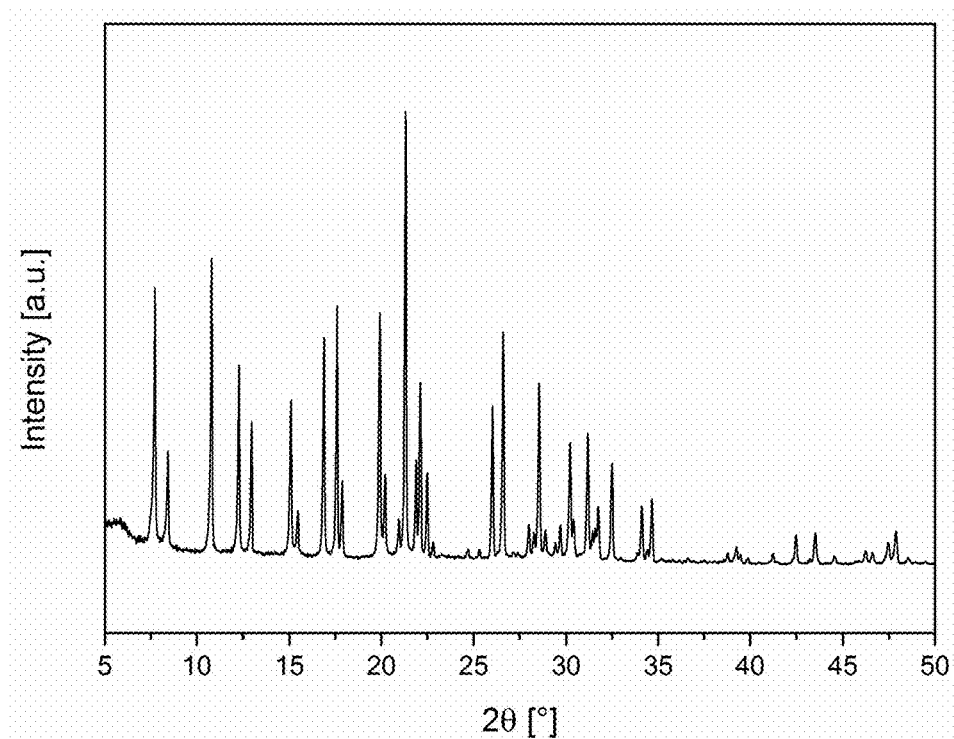
FIG. 1 is an XRD diffraction pattern of a sample of SAPO STA-18AP as prepared in Example 4.

As used in this specification and the claims, the singular forms "a", "an" and "the" include plural referents unless the context clearly indicates otherwise. Thus, for example, reference to "a catalyst" includes a mixture of two or more catalysts, and the like.

As used herein, the term "SFW" refers to an SFW topological type as recognized by the International Zeolite Association (IZA) Structure Commission. Other crystalline phases may also be present, but the primary crystalline phase comprises ≥about 90 weight percent SFW, preferably ≥about 95 weight percent SFW, and even more preferably ≥about 97 or ≥about 99 weight percent SFW. Preferably, the SFW molecular sieve is substantially free of other crystalline phases and is not an intergrowth of two or more framework types. By "substantially free" with respect to other crystalline phases, it is meant that the molecular sieve contains ≥99 weight percent SFW.

STA-18 refers a material having an SFW framework with phosphate within the framework.

STA-18AP refers to as-prepared material having an SFW framework with phosphate within the framework and containing one or more structure directing agents (SDA).

STA-18C refers to a calcined molecular sieve having an SFW framework with phosphate within the framework. STA-18C can be prepared by calcining STA-18AP as described below.

The term "calcine", or "calcination", means heating the material in air or oxygen. This definition is consistent with the IUPAC definition of calcination. (IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook.) Calcination is performed to decompose a metal salt and promote the exchange of metal ions within the catalyst and also to adhere the catalyst to a substrate. The temperatures used in calcination depend upon the components in the material to be calcined and generally are between about 400° C. to about 900° C. for approximately 1 to 8 hours. In some cases, calcination can be performed up to a temperature of about 1200° C. In applications involving the processes described herein, calcinations are generally performed at temperatures from about 400° C. to about 700° C. for approximately 1 to 8 hours, preferably at temperatures from about 400° C. to about 650° C. for approximately 1 to 4 hours.

The term "about" means approximately and refers to a range that is optionally ±25%, preferably ±10%, more preferably, ±5%, or most preferably ±1% of the value with which the term is associated.

The term "substantially similar", when used to describe a comparison of a diffraction pattern, means that the locations of one or more peaks, in degrees 2-theta, and the intensity of these peaks can vary based on experimental variability due to the instrumentation used, the conditions under which the diffraction pattern was obtained, and impurities that may be present in a sample.

When a range, or ranges, for various numerical elements are provided, the range, or ranges, can include the values, unless otherwise specified.

In a first aspect of the invention, provided is a novel calcined molecular sieve, STA-18C, comprising an SFW type framework having phosphate within the framework. STA-18C was prepared by calcining STA-18AP (as-prepared) that contains structure directing agents. The structure directing agents are preferably a 1,4-diazabicyclo [2.2.2] octane derivative (SDA1) and a lower alkyl amine (SDA2).

STA-18 can be a silicoaluminophosphate (SAPO), a metal silicoaluminophosphate (MeSAPO) or a metal aluminophosphate (MeAPO). The molecular sieve is preferably a silicoaluminophosphate.

SAPO STA-18 and MeSAPO STA-18 can have the molar relationship: $(Si_xAl_yP_z)O_2$, where x is the mole fraction of Si and has a value from 0.05 to 0.3, preferably from 0.1 to 0.15, y is the mole fraction of Al and has a value from 0.4 to 0.6, preferably from 0.45 to 0.5, z is the mole fraction of P and has a value from 0.2 to 0.45, preferably from 0.3 to 0.35 and x+y+z=1, where the endpoints are preferably included.

MeAPO STA-18 can have the molar relationship: $(M^{2+}{}_xAl_yP_z)O_2$, where x is the mole fraction of $M^{2+}$ and has a value from 0.01 to 0.5, y is the mole fraction of Al and has a value from 0.01 to 0.5, and z is the mole fraction of P and has a value from 0.01 to 0.5, and x+y+z=1, where the endpoints are preferably included.

The molecular sieve can comprise at least one metal within the framework where the metal is selected from at least one of the metals of Groups of the Periodic Table IIIA, IB, IIB, VA, VIA, VIIA, VIIIA and combinations thereof, preferably cerium, chromium, cobalt, copper, iron, magnesium, manganese, molybdenum, nickel, palladium, platinum, rhodium, titanium, tungsten, vanadium and zinc, more preferably copper, iron, palladium, platinum, vanadium and zinc.

The structure of SAPO STA-18 was determined by x-ray analysis. The x-ray patterns presented in the following examples were obtained using standard x-ray powder diffraction techniques. The X-ray powder diffraction data was obtained with a Panalytical Empyrean automated diffractometer equipped with a X'Celerator detector. Measurements were made with automatic slit divergence. The data were collected in Bragg-Brentano geometry, using Cu $K\alpha_1$ X-radiation from an X-ray tube operating at 45 KV and 35 mA. The radiation was monochromatised. Step scanned data were collected between 5 and 50 degrees 2theta with step size 0.01°, time step$^{-1}$ 160 s, rad soller 0.04, 45 kV, 35 mA. The collected data were analysed with DIFFRAC.SUITE EVA Bruker software. The X-ray computer intensities given herein are based on peak height.

The relative intensities, 100 $I/I_0$, where $I_0$ is the intensity of the strongest line or peak, and d, the interplanar spacing in Angstroms corresponding to the recorded lines, were calculated. The X-ray diffraction pattern of Table 1 is characteristic of all species of STA-18C family compositions. Minor variations in the diffraction patterns of STA-18C and STA-18AP in the tables or figures can also result from variations in the organic compound used in the preparation and from variations in the Si, Al and P mole ratios from sample to sample. Notwithstanding these minor perturbations, the basic crystal structures for the as-prepared condition and the calcined condition remain substantially unchanged. Similar variations can also be found in the X-ray diffraction patterns of various STA-18AP materials.

As will be understood by those of skill in the art, the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of 100× $I/I_0$, the above designations are defined as: w (weak)<20; m (medium) is ≥20 and <40; s (strong) is ≥40 and <60; and vs (very strong) is ≥60. When the intensity is near the endpoint for a range, the intensity may be characterized was being in either of the ranges. For example, intensities of 18-22 may be listed as w-m. However, due to variations in intensity of the lines, as known in the art, one or more of the lines may have an intensity that is in an adjacent range.

The powder XRD of SAPO STA-18C is shown in FIGS. 4, 6, 8 and 10. The characteristic lines are shown in Table 1.

TABLE 1

Diffraction peaks of SAPO STA-18C (calcined)

| d-spacing [Å] | 2θ [°] | Rel. Int. [%] |
|---|---|---|
| 11.35 | 7.8 | vs |
| 10.37 | 8.5 | m |
| 8.07 | 11.0 | vs |
| 7.09 | 12.5 | m |
| 6.80 | 13.0 | vs |
| 5.84 | 15.2 | w |
| 5.20 | 17.0 | m |
| 4.94 | 17.9 | m |
| 4.43 | 20.0 | m |
| 4.36 | 20.3 | w |
| 4.14 | 21.5 | s |
| 3.98 | 22.3 | m |
| 3.41 | 26.2 | m |
| 3.29 | 27.1 | w |
| 3.14 | 28.4 | w |
| 3.07 | 29.0 | w |
| 2.94 | 30.4 | m |
| 2.85 | 31.4 | w |
| 2.80 | 31.9 | w |
| 2.72 | 33.0 | w |
| 2.58 | 34.8 | w |

The XRD diffraction pattern of the calcined product is similar to other molecular sieves having an SFW type structure. However, the catalytic properties of STA-18C are distinct from those of other molecular sieves having an SFW structure because STA-18 has a new composition based on a silicoaluminophosphate framework SAPO STA-18C can have at least one property selected from the group consisting of: a characteristic X-ray powder diffraction pattern substantially similar to that shown in FIG. 4; and a characteristic X-ray powder diffraction pattern comprising 2-theta positions at 7.8 (vs), 11.0 (vs), 13.0 (vs) and 21.5 (s)±0.2 with the corresponding relative intensity shown in parenthesis, where the corresponding relative intensities are w (weak)<20; m (medium) is ≥20 and <40; s (strong) is ≥40 and <60; and vs (very strong) is ≥60.

The characteristic X-ray powder diffraction pattern can further comprise a characteristic X-ray powder diffraction pattern comprising one or more lines, preferably two or more lines, more preferably three or more lines, even more preferably four or more lines at 2-theta positions at 8.5 (m), 12.5 (m), 17.0 (m), 17.9 (m-s), 20.0 (m), 22.3 (m), 26.2 (m) and 30.4 (m)±0.2 with the corresponding relative intensity shown in parenthesis.

The characteristic X-ray powder diffraction pattern can further comprise a characteristic X-ray powder diffraction pattern comprising one or more lines, preferably two or more lines, more preferably three or more lines, even more preferably four or more lines at 2-theta positions at 15.2 (w), 20.3 (w), 27.1 (w), 28.4 (w), 29.0 (w), 31.4 (w-m), 31.9 (w), 33.0 (w) and 34.8 (w)±0.2 with the corresponding relative intensity shown in parenthesis.

The unit cell of calcined, dehydrated STA-18 is described by the following:

| Unit cell | |
|---|---|
| Chemical formula | $Al_{54}P_{40.5}Si_{13.5}O_{216}$ |
| Crystal system | trigonal |
| Space group | R-3 |
| a/Å | 13.79540(18) |
| b/Å | 13.79540(18) |
| c/Å | 44.6461(15) |
| Volume/Å$^3$ | 7358.40(24) |

The SFW structure in the molecular sieve of the first aspect of the invention can be free from structural faulting.

In a second aspect of the invention, provided is a method of manufacturing a molecular sieve of the first aspect of the invention (STA-18C), preferably in substantially pure form. STA-18C can be produced by calcining an STA-18AP molecular sieve comprising one or more SDAs at a temperature and for a period of time sufficient to remove the template and form STA-18C. STA-18AP can be calcined at 300-700° C., preferably at 400 to 650° C. in the presence of an oxygen-containing gas (such as air) when it is desirable to oxidize the SDAs. In some case, where a reducing environment is preferred, calcination is performed using an inert gas. The inert gas can be any gas that is substantially free of oxygen (less than 1 vol. % oxygen, preferably less than 0.1 vol. % oxygen), most preferably oxygen-free. Preferably, the inert gas is nitrogen, argon, neon, helium, carbon dioxide, or the like, and mixture thereof. The calcination is preferably performed for greater than 1 hour.

The method of manufacturing STA-18C can further comprise the steps of forming STA-18AP, as described below. The method of forming STA-18AP generally comprises: (i) forming and heating a reaction mixture comprising: (a) at least one source of alumina, (b) at least one source of silica, (c) at least one source of phosphorus, and (d) one or more structure directing agents (SDAs); (ii) forming molecular sieve crystals having a SFW framework and the structure directing agent, and (iii) recovering at least a portion of the molecular sieve crystals from the reaction mixture.

STA18-AP

STA-18AP can be a silicoaluminophosphate (SAPO), a metal silicoaluminophosphate (MeSAPO) or a metal aluminophosphate (MeAPO). Preferably the molecular sieve is a SAPO. STA-18AP contains one or more structure directing agents. The structure directing agents preferably comprise a 1,4-diazabicyclo[2.2.2]octane derivative (SDA1) and a lower alkyl amine (SDA2). The 1,4-diazabicyclo[2.2.2]octane derivative (SDA1) can be a 1,6-(1,4-diazabicyclo [2.2.2] octane)hexyl cation, a 1,7-(1,4-diazabicyclo[2.2.2] octane)heptyl cation or a 1,8-(1,4-diazabicyclo [2.2.2]octane)octyl cation. Each alkyl group in a lower alkyl amine (SDA2) can contain from 1 to 6 carbon atoms. The lower alkyl amine is preferably trimethylamine or N,N-dimethylethylamine.

The powder XRD of a SAPO STA-18AP comprising 1,6-(1,4-diazabicyclo[2.2.2] octane)hexyl cations and trimethylamine is shown in FIG. 1. The characteristic lines are shown in Table 2 where the degrees 2θ is ±0.2 and the relative intensity is based on the strongest line in the X-ray pattern which is assigned a value of 100. W (weak) is <20; m (medium) is ≥20 and <40; s (strong) is ≥40 and <60; and vs (very strong) is ≥60. When a characteristic line is present near an end point for one of these ranges, variations in the intensity of the line due to various known experimental factors, including the presence of impurities and the instrument used, can result in the intensity being in the adjacent range. Therefore, this line can be described as being a combination of two ranges. For example, a line with an intensity of 18 is at the upper end of a weak range, but a small variation could result in the intensity being in the range of about 20-25. In this case the intensity range could be reported as being w-m.

TABLE 2

Diffraction peaks of as prepared SAPO STA-18AP made using diDABCO-C6 and trimethylamine

| d-spacing [Å] | 2θ [°] | Rel. Int. [%] |
|---|---|---|
| 11.44 | 7.7 | vs |
| 10.48 | 8.4 | m |
| 8.19 | 10.8 | vs |
| 7.20 | 12.3 | s |
| 6.84 | 12.9 | m |
| 5.87 | 15.1 | m |
| 5.73 | 15.5 | w |
| 5.25 | 16.9 | s |
| 5.04 | 17.6 | s |
| 4.96 | 17.9 | w |
| 4.46 | 19.9 | s |
| 4.39 | 20.2 | w |
| 4.24 | 20.9 | w |
| 4.17 | 21.3 | vs |
| 4.06 | 21.9 | m |
| 4.02 | 22.1 | m |
| 3.95 | 22.5 | m |
| 3.42 | 26.0 | m |
| 3.35 | 26.6 | s |
| 3.19 | 28.0 | w |
| 3.16 | 28.2 | w |
| 3.13 | 28.5 | m |
| 3.09 | 28.9 | w |
| 3.01 | 29.7 | w |
| 2.96 | 30.2 | m |
| 2.94 | 30.4 | w |
| 2.87 | 31.2 | m |
| 2.83 | 31.6 | w |
| 2.82 | 31.7 | w |
| 2.76 | 32.5 | w |
| 2.63 | 34.1 | w |
| 2.59 | 34.7 | w |

SAPO STA-18AP comprising 1,6-(1,4-diazabicyclo [2.2.2] octane)hexyl cations and trimethylamine has at least one property selected from the group consisting of: a characteristic X-ray powder diffraction pattern substantially similar to that shown in FIG. 1; and a characteristic X-ray powder diffraction pattern comprising 2-theta positions at 7.7 (vs), 10.8 (vs), 12.3 (s), 16.9 (s), 17.6 (s), 19.9 (s), 21.3 (vs) and 26.6 (m), where the 2-theta position are ±0.2 and the corresponding relative intensity are shown in parenthesis, where the corresponding relative intensities are w (weak) <20; m (medium) is ≥20 and <40; s (strong) is ≥40 and <60; and vs (very strong) is ≥60.

The characteristic X-ray powder diffraction pattern can further comprise a characteristic X-ray powder diffraction pattern comprising one or more lines, preferably two or more lines, more preferably three or more lines, even more preferably four or more lines at 2-theta positions at 8.4 (m), 12.9 (m), 15.1 (m-s), 21.9 (w-m), 22.1 (m-s), 22.5 (w-m), 26.0 (m-s), 28.5 (m-s), 30.2 (m) and 31.2 (m)±0.2 with the corresponding relative intensity shown in parenthesis.

The characteristic X-ray powder diffraction pattern can further comprise a characteristic X-ray powder diffraction pattern comprising one or more lines, preferably two or more lines, more preferably three or more lines, even more preferably four or more lines at 15.5 (w), 17.9 (w-m), 20.2 (w-m), 20.9 (w), 28.0 (w), 28.2 (w), 28.9 (w), 29.7 (w), 30.4 (w), 31.6 (w), 31.7 (w), 32.5 (w-m), 34.1 (w) and 34.7 (w)±0.2 with the corresponding relative intensity shown in parenthesis.

Figure 2:
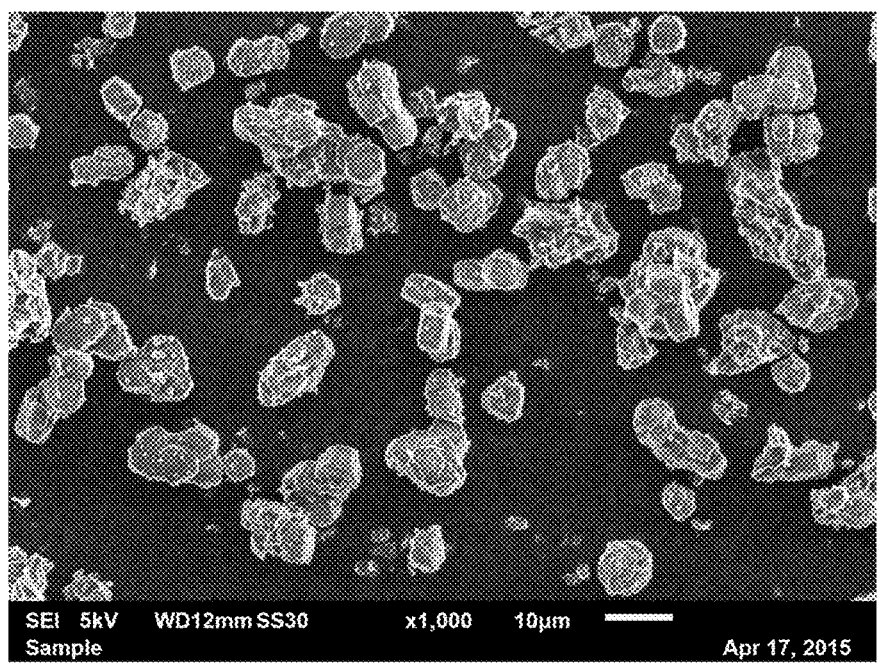
FIG. 2 is an SEM micrograph of a sample of a SAPO STA-18AP as prepared in Example 4.
Figure 3:
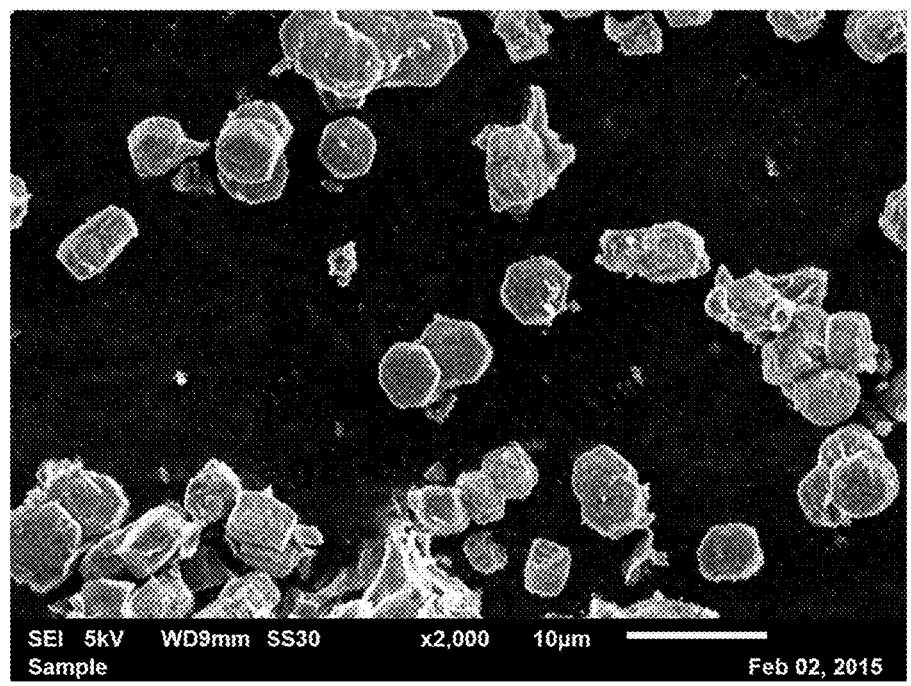
FIG. 3 is an SEM micrograph of a sample of a SAPO STA-18AP as prepared in Example 4.

Scanning electron microscope (SEM) images of SAPO-STA-18AP of Example 4 were collected using a JEOL JSM 6010LA SEM. The crystals have a hexagonal prismatic morphology with side of length between 5-10 μm and about 2 μm thick. (FIGS. 2 and 3).

Figure 5:
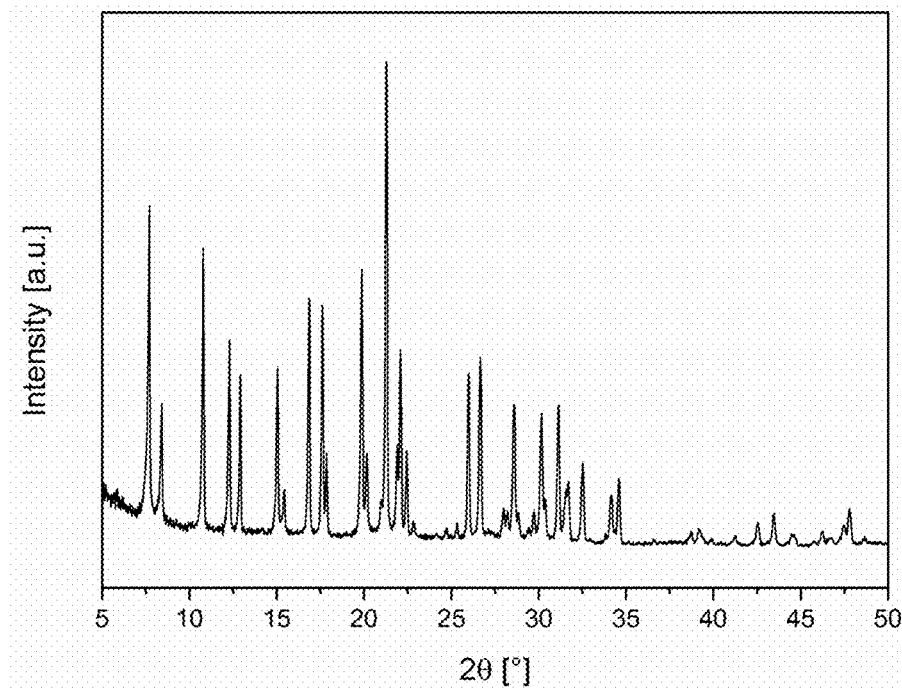
FIG. 5 is an XRD diffraction pattern of a sample of SAPO STA-18AP as prepared in Example 6.

SAPO STA-18AP can comprise 1,7-(1,4-diazabicyclo [2.2.2] octane)heptyl cations (formed from diDABCO-C7) and trimethylamine as SDAs. The powder XRD of this molecular sieve is shown in FIG. 5. The characteristic lines are shown in Table 3.

TABLE 3

Diffraction peaks of as prepared SAPO STA-18AP made using trimethylamine and diDABCO-C7

| d-spacing [Å] | 2θ [°] | Rel. Int. [%] |
|---|---|---|
| 11.47 | 7.7 | vs |
| 10.50 | 8.4 | m |
| 8.19 | 10.8 | vs |
| 7.20 | 12.3 | s |
| 6.85 | 12.9 | m |
| 5.89 | 15.1 | m |
| 5.74 | 15.4 | w |
| 5.26 | 16.9 | s |
| 5.03 | 17.6 | s |
| 4.97 | 17.9 | w |
| 4.46 | 19.9 | s |
| 4.40 | 20.2 | w |
| 4.24 | 21.0 | w |
| 4.17 | 21.3 | vs |
| 4.06 | 21.9 | m |
| 4.02 | 22.1 | m |
| 3.96 | 22.4 | m |
| 3.43 | 26.0 | m |
| 3.34 | 26.7 | s |
| 3.19 | 28.0 | w |
| 3.16 | 28.2 | w |
| 3.12 | 28.6 | m |
| 3.10 | 28.8 | w |
| 3.00 | 29.7 | w |
| 2.96 | 30.2 | m |
| 2.94 | 30.4 | w |
| 2.87 | 31.1 | m |
| 2.84 | 31.5 | w |
| 2.82 | 31.7 | w |
| 2.75 | 32.5 | w |
| 2.62 | 34.2 | w |
| 2.59 | 34.6 | w |

SAPO STA-18AP comprising 1,7-(1,4-diazabicyclo [2.2.2] octane)heptyl cations and trimethylamine has at least one property selected from the group consisting of: a characteristic X-ray powder diffraction pattern substantially similar to that shown in FIG. 5; and a characteristic X-ray powder diffraction pattern comprising 2-theta positions at 7.7 (vs), 10.8 (s-vs), 12.3 (m-s), 16.9 (s), 17.6 (s), 19.9 (s-vs), 21.3 (vs) and 26.7 (m-s)±0.2 with the corresponding relative intensity shown in parenthesis, where the corresponding relative intensities are w (weak)<20; m (medium) is ≥20 and <40; s (strong) is ≥40 and <60; and vs (very strong) is ≥60.

The characteristic X-ray powder diffraction pattern can further comprise a characteristic X-ray powder diffraction pattern comprising one or more lines, preferably two or more lines, more preferably three or more lines, even more preferably four or more lines at 2-theta positions at 8.4 (m), 12.9 (m-s), 15.1 (m-s), 21.9 (w-m), 22.1 (m-s), 22.4 (m-s), 26.0 (m-s), 28.6 (m), 30.2 (s) and 31.1 (m-s)±0.2 with the corresponding relative intensity shown in parenthesis.

The characteristic X-ray powder diffraction pattern can further comprise a characteristic X-ray powder diffraction pattern comprising one or more lines, preferably two or more lines, more preferably three or more lines, even more preferably four or more lines at 2-theta positions at 15.4 (w), 17.9 (w-m), 20.2 (w-m), 21.0 (w), 28.0 (w), 28.2 (w), 28.8 (w), 29.7 (w), 30.4 (w), 31.5 (w), 31.7 (w), 32.5 (w-m), 34.2 (w) and 34.6 (w)±0.2 with the corresponding relative intensity shown in parenthesis.

Figure 7:
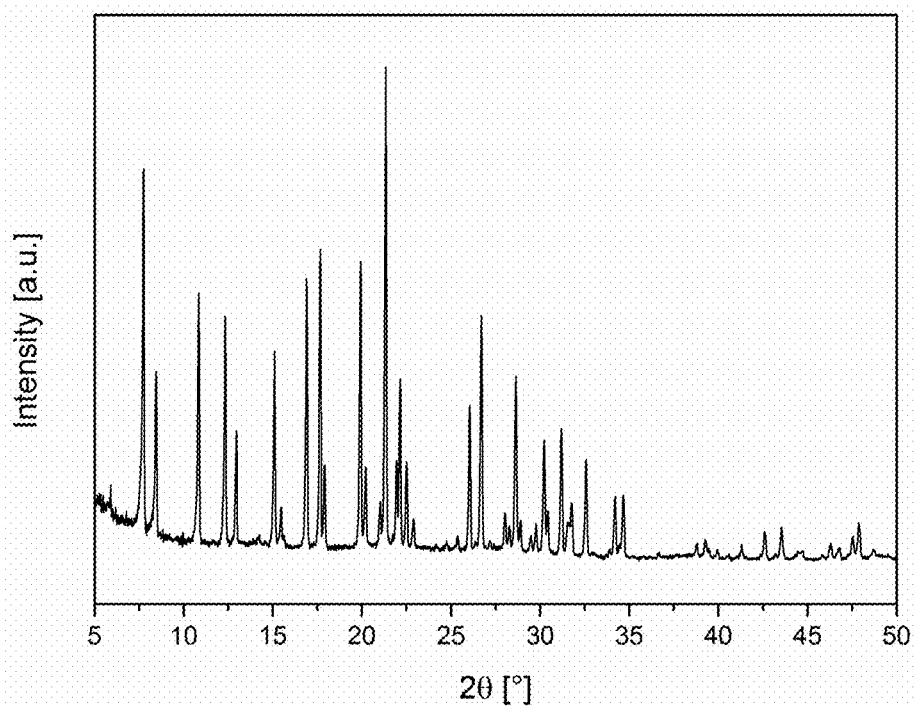
FIG. 7 is an XRD diffraction pattern of a sample of SAPO STA-18AP as prepared in Example 8.

SAPO STA-18AP can comprise trimethylamine and 1,8-(1,4-diazabicyclo[2.2.2] octane)octyl cations (formed from diDABCO-C8) and trimethylamine as SDAs. The powder XRD of SAPO STA-18AP comprising 1,8-(1,4-diazabicyclo [2.2.2]octane)octyl cations and trimethylamine is shown in FIG. 7. The characteristic lines are shown in Table 4.

TABLE 4

Diffraction peaks of as prepared SAPO STA-18AP made using diDABCO-C8 and trimethylamine

| d-spacing [Å] | 2θ [°] | Rel. Int. [%] |
|---|---|---|
| 11.40 | 7.8 | vs |
| 10.45 | 8.5 | m |
| 8.16 | 10.8 | vs |
| 7.17 | 12.3 | s |
| 6.83 | 13.0 | m |
| 5.87 | 15.1 | m |
| 5.72 | 15.5 | w |
| 5.24 | 16.9 | s |
| 5.02 | 17.7 | s |
| 4.95 | 17.9 | w |
| 4.45 | 19.9 | s |
| 4.39 | 20.2 | w |
| 4.22 | 21.0 | w |
| 4.16 | 21.4 | vs |
| 4.05 | 22.0 | m |
| 4.01 | 22.2 | m |
| 3.95 | 22.5 | m |
| 3.42 | 26.1 | m |
| 3.34 | 26.7 | s |
| 3.18 | 28.0 | w |
| 3.16 | 28.3 | w |
| 3.12 | 28.6 | m |
| 3.09 | 28.9 | w |
| 3.00 | 29.8 | w |
| 2.96 | 30.2 | m |
| 2.94 | 30.4 | w |
| 2.87 | 31.2 | m |
| 2.84 | 31.5 | w |
| 2.82 | 31.8 | w |
| 2.75 | 32.6 | w |
| 2.62 | 34.2 | w |
| 2.59 | 34.7 | w |

SAPO STA-18AP comprising trimethylamine and 1,8-(1,4-diazabicyclo[2.2.2] octane)octyl cations has at least one property selected from the group consisting of: a characteristic X-ray powder diffraction pattern substantially similar to that shown in FIG. 7; and a characteristic X-ray powder diffraction pattern comprising 2-theta positions at 7.8 (vs), 10.8 (s), 12.3 (s), 16.9 (s), 17.7 (s-vs), 19.9 (v-vs), 21.4 (vs) and 26.7 (s)±0.2 with the corresponding relative intensity shown in parenthesis, where the corresponding relative intensities are w (weak)<20; m (medium) is ≥20 and <40; s (strong) is ≥40 and <60; and vs (very strong) is ≥60.

The characteristic X-ray powder diffraction pattern can further comprise a characteristic X-ray powder diffraction pattern one or more lines, preferably two or more lines, more preferably three or more lines, even more preferably four or more lines at comprising 2-theta positions at 8.5 (m-s), 13.0 (m), 15.1 (m-s), 22.0 (w-m), 22.2 (m-s), 22.5 (w-m), 26.1 (m), 28.6 (m-s), 30.2 (m) and 31.2 (m)±0.2 with the corresponding relative intensity shown in parenthesis.

The characteristic X-ray powder diffraction pattern can further comprise a characteristic X-ray powder diffraction pattern comprising one or more lines, preferably two or more lines, more preferably three or more lines, even more preferably four or more lines at 2-theta positions at 15.5 (w), 17.9 (w-m), 20.2 (w-m), 21.0 (w), 28.0 (w), 28.3 (w), 28.9 (w), 29.9 (w), 30.4 (w), 31.5 (w), 31.8 (w), 32.6 (w-m), 34.2 (w) and 34.7 (w)±0.2 with the corresponding relative intensity shown in parenthesis.

The method of forming STA-18AP generally comprises: (i) forming and heating a reaction mixture comprising: (a) at least one source of alumina, (b) at least one source of silica, (c) at least one source of phosphorus, and (d) one or more structure directing agents (SDAs); (ii) forming molecular sieve crystals having a SFW framework and the structure directing agent, and (iii) recovering at least a portion of the molecular sieve crystals from the reaction mixture.

The mixture comprising a silicon component, an aluminum component, a phosphorus component, and a structure directing agent can go through an optional aging period before being subjected to a hydrothermal treatment at an elevated temperature. The product formed from the hydrothermal treatment contains the SDAs. This product can be calcined at an elevated temperature to remove the two SDAs and form STA-18C.

A number of silicon compounds and their mixtures can be used as the silicon component for the method of the present invention. The silicon compounds include, but are not limited to silica sol silica gel, colloidal silica, fumed silica, silicic acid, tetraethyl silicate, tetramethyl silicate, and mixtures thereof. A preferred silicon component comprises a material selected from the group consisting of silica sol, silica gel, colloidal silica, fumed silica, silicic acid, and mixtures thereof.

Many aluminum compounds and their mixtures are suitable for use as the aluminum component in the present invention. The aluminum compounds include, but are not necessarily limited to aluminum oxide, boehmite, pseudo boehmite, aluminum hydroxy chloride, aluminum alkoxides such as aluminum tri-isopropoxide, aluminum tri-ethoxide, aluminum tri-n-butoxide and aluminum tri-isobutoxide, and mixtures thereof. A preferred aluminum component comprises a material selected from the group consisting of aluminum hydroxide, boehmite and pseudo boehmite.

The phosphorus compounds suitable for use as the phosphorus component include, but are not necessarily limited to, orthophosphoric acid, phosphorus acid, trimethyl phosphate, triethyl phosphate, and mixtures thereof. A preferred phosphorus component comprises orthophosphoric acid ($H_3PO_4$). Another preferred phosphorus component comprises the commercially available 85 wt % phosphoric acid (in water). Alternately, phosphorus oxides ($P_2O_3$, $P_2O_5$, and $POCl_3$) can be used, preferably after they are dissolved in a suitable solvent such as water.

A suitable organic template comprises a 1,4-diazabicyclo [2.2.2]octane derivative (SDA1) and a lower alkyl amine (SDA2). The 1,4-diazabicyclo [2.2.2]octane derivative (SDA1) comprises a 1,6-(1,4-diazabicyclo[2.2.2]octane) hexyl cation, a 1,7-(1,4-diazabicyclo[2.2.2]octane)heptyl cation or a 1,8-(1,4-diazabicyclo[2.2.2]octane)octyl cation. The corresponding anions can be acetate, bicarbonate, bromide, carbonate, carboxylate, chloride, fluoride, hydroxide, iodide, sulfate and tetrafluoroborate, preferably bromide. Preferably the 1,4-diazabicyclo [2.2.2]octane derivative (SDA1) is 1,6-(1,4-diazabicyclo [2.2.2]octane)hexyl dibromide (diDABCO-C6), 1,7-(1,4-diazabicyclo[2.2.2]octane) heptyl dibromide (diDABCO-C7) or 1,8-(1,4-diazabicyclo [2.2.2] octane)octyl dibromide (diDABCO-C8).

The lower alkyl amine (SDA2) is preferably trimethylamine or N,N-dimethylethylamine, more preferably trimethyl amine. When N,N-dimethylethylamine is used, AlPO-5 is present in the product as an impurity.

A solvent can be mixed with the organic template before the template is added to the reaction mixture. Preferably, the organic template is completely mixable with, or soluble in, the solvent. Suitable solvents include but are not necessarily limited to water, methanol, ethanol, n-propanol, iso-propanol, $C_4$ alcohols, ethylene glycol, 1,2-propylene glycol, 1,3-propylene glycol and mixtures thereof. A preferred solvent comprises water.

The silica component and the phosphorus component can be mixed in a suitable solvent to form a first mixture of uniform composition and texture. Adequate mixing, stirring, or agitation usually can be used. The aluminum component can be added to this mixture, followed by the first organic template (SDA1), a 1,4-diazabicyclo[2.2.2]octane derivative, preferably 1,6-(1,4-diazabicyclo[2.2.2] octane)hexyl dibromide (diDABCO-C6) or 1,7-(1,4-diazabicyclo[2.2.2] octane)heptyl dibromide (diDABCO-C7) or 1,8-(1,4-diazabicyclo [2.2.2]octane)octyl dibromide (diDABCO-C8). A lower alkyl amine (SDA2), such as trimethylamine, can then be added and the mixture can be stirred for several minutes, then a lower alkyl ammonium hydroxide can be added to control the pH. Lower alkyl ammonium hydroxide comprises one or more alkyl groups where each alkyl group can contain from 1 to 8 carbon atoms. Preferably the lower alkyl ammonium hydroxide is tetrabutylammonium hydroxide, tetraethylammonium hydroxide, tetrapropylammonium hydroxide, tetrapenthylammonium hydroxide or tetrahexylammonium hydroxide, more preferably tetrabutylammonium hydroxide, which allowed for the synthesis of pure STA-18.

In order to make a molecular sieve comprising STA-18, the molar ratios of the components in the mixture must be controlled and maintained. Before being subjected to conditions effective to produce the molecular sieve product, the final reaction mixture, excluding any other organic or inorganic moieties or species which may be present, has a molar compositional ratio of:

| | |
|---|---|
| P/A | 0.5-0.99 |
| $MeO_2$/A | 0.02-1.0 |
| SDA1 (1,4-diazabicyclo[2.2.2]octane derivative)/A | 0.1-0.6 |
| SDA2 (lower alkyl amine)/A | 0.1-0.6 |
| Lower alkyl ammonia hydroxide/A | 0.1-0.6 |
| $H_2O$/A | 20-200 | where P the source of phosphorous and is calculated as being in the oxide form ($P_2O_5$), A is Al, Fe, Cr, B, Ga or combinations thereof and is calculated as being in the oxide form ($A_2O_3$); and Me is Si, Ge, Mg or combinations thereof and is calculated as being in the oxide form ($MO_2$).

The molar ratio of P to A can be in the range of from about 0.5 to about 0.99, preferably from about 0.55 to about 0.75, more preferably from about 0.68 to about 0.71, where the endpoints can be included.

The molar ratio of $MeO_2$ to A can be in the range of from about 0.02 to about 1.0, preferably from about 0.01 to about 1.0, more preferably from about 0.5 to about 0.9, even more preferably from about 0.58 to about 0.75, where the endpoints can be included.

The molar ratio of STA1, a 1,4-diazabicyclo [2.2.2]octane derivative to A can be in the range of from about 0.1 to about 0.60, preferably from about 0.20 to about 0.3, where the endpoints can be included.

The molar ratio of STA2, a lower alkyl amine to A can be in the range of from about 0.1 to about 0.60, preferably from about 0.20 to about 0.3, where the endpoints can be included.

The molar ratio of a lower alkyl ammonium hydroxide to A can be in the range of from about 0.1 to about 0.60, preferably from about 0.20 to about 0.3, where the endpoints can be included.

The molar ratio of water to A can be in the range of from about 20 to about 200, preferably from about 60 to about 120, more preferably about 70 to about 90, where the endpoints can be included.

It is preferable that the pH value of the final reaction mixture be in the range from about 5.5 to about 8.5, preferably from about 6.5 to about 7.5, where the endpoints can be included. The pH value of a mixture can be adjusted, if desired, by adding an appropriate amount of a base, preferably a lower alkyl amine such as tetrabutylammonium hydroxide.

When the STA-18 is a SAPO, the final reaction mixture, excluding any other organic or inorganic moieties or species which may be present is characterized by the general formula as follows:

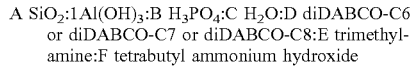

A SiO$_2$:1Al(OH)$_3$:B H$_3$PO$_4$:C H$_2$O:D diDABCO-C6
or diDABCO-C7 or diDABCO-C8:E trimethyl-
amine:F tetrabutyl ammonium hydroxide The molar ratio of silicon to aluminum hydroxide can be in the range of from about 0.10 to about 0.50, preferably from about 0.25 to about 0.45, more preferably from about 0.29 to about 0.32, where the endpoints may be included.

The molar ratio of aluminum hydroxide to H$_3$PO$_4$ can be in the range of from about 0.5 to about 0.9, preferably from about 0.55 to about 0.75, more preferably from about 0.68 to about 0.71, where the endpoints may be included.

The molar ratio of aluminum hydroxide to water can be in the range of from about 10 to about 100, preferably from about 30 to about 60, more preferably about 35 to about 45, where the endpoints may be included.

The molar ratio of aluminum hydroxide to diDABCO-C6 or diDABCO-C7 or diDABCO-C8 can be in the range of from about 0.05 to about 0.30, preferably from about 0.10 to about 0.15, where the endpoints may be included.

The molar ratio of aluminum hydroxide to trimethylamine can be in the range of from about 0.05 to about 0.5, preferably from about 0.1 to about 0.2, more preferably about 0.12 to 0.15, where the endpoints may be included.

The molar ratio of aluminum hydroxide to tetrabutylammonium hydroxide can be in the range of from about 0.1 to about 0.5, preferably from about 0.15 to about 0.35, more preferably from about 0.25 to about 0.3, where the endpoints may be included.

It is preferable that the pH value of the final reaction mixture be in the range from about 5.5 to about 8.5, preferably from about 6.5 to about 7.5, where the endpoints can be included. The pH value of a mixture can be adjusted, if desired, by adding an appropriate amount of a base such as a lower alkyl amine like tetrabutylammonium hydroxide.

It is preferable to use adequate mixing, blending, stirring, or agitation to provide a uniform composition throughout the mixture. The use of a concentration or composition gradient should be minimized because such a gradient could result in the formation of different molecular sieve products.

Preferably, a constant temperature is maintained during the preparation of the mixture. Cooling or heating may be required to provide a constant temperature environment. A suitable temperature for preparation of a mixture can be in the range of from about 20° C. to about 80° C., preferably from about 25° C. to about 50° C., where the endpoints can be included. Pressure is usually not critical for preparing a mixture unless one or more gases are used to control other reaction parameters, such as pH, temperature, or concentration.

Preferably, the overall process will have an overall yield on silica of ≥about 60%, for example ≥about 70%, ≥about 80%. Preferably, the overall process will have an overall yield on SDA of ≥about 40%, for example ≥about 60%, ≥about 80%, ≥about 90%, about 40-90%, about 40-60%, about 60-80%, about 80-90%, about 90-95%, or about 95-99%.

The reaction mixture can be in the form of a solution, a colloidal dispersion (colloidal sol), gel, or paste, with a gel being preferred.

Generally, the reaction mixture can be maintained at an elevated temperature until the STA-18 crystals are formed. The hydrothermal crystallization can be usually conducted under autogenous pressure, at a temperature between about 120-220° C., for example between about 150 and 200° C., for duration of several hours, for example, about 0.1-10 days, and preferably from about 1-7 days.

During the hydrothermal crystallization step, crystals of STA-18 can be allowed to nucleate spontaneously from the reaction mixture. The use of SAPO-56 crystals or other AFX containing materials or more generally other ABC-6 framework structure materials in which the repeated stacking sequence can be described using only double-6-rings (D6Rs), such as AFT, GME and SFW, as seed material can be advantageous in decreasing the time necessary for complete crystallization to occur. When used as seeds, SAPO-56 or other AFX containing crystals or other materials which framework belongs to the ABC-6 family, preferably those in which the repeated stacking sequence can be described using double-6-rings (i.e. AFT, GME, SFW) can be added in an amount between 0.1 and 10% of the weight of silica used in the reaction mixture.

Once the STA-18 crystals have formed, the solid product can be separated from the reaction mixture by standard separation techniques such as filtration. The STA-18 crystals are water-washed and then dried, for several second to a few minutes (e.g., 5 second to 10 minutes for flash drying) or several hours (e.g., about 4-24 hours for oven drying at 75-150° C.), to obtain as-synthesized STA-18 crystals having a SFW topological type framework and an SDA within the crystals. The drying step can be performed at atmospheric pressure or under vacuum.

It will be appreciated that the foregoing sequence of steps, as well as each of the above-mentioned periods of time and temperature values are merely exemplary and can be varied.

The STA-18 zeolite crystals produced in accordance with this process can be uniform, with little to no twinning and/or multiple twinning or may form agglomerates.

The STA-18 crystals produced in accordance with the methods described herein can have a mean crystalline size of about 0.01 to about 50 μm, for example about 0.5 to about 20 μm, about 0.1 to about 10 μm, and about 1 to about 5 μm, where the endpoints can be included. Large crystals can be milled using a jet mill or other particle-on-particle milling technique to an average size of about 1.0 to about 1.5 micron to facilitate washcoating a slurry containing the catalyst to a substrate, such as a flow-through monolith.

The reaction mixture for the STA-18AP synthesis process typically contains at least one source of aluminum, at least one source of phosphorous, at least one source of silicon, at least two SDAs (SDA1 and SDA2) useful in forming STA-18, and at least one source of a co-base, preferably a lower alkyl amone. It is understood, however, that the synthesis method described herein is not necessarily limited to silicoaluminophosphates, but can also be applied to synthesize other molecular sieves having an SFW structure, such as (but not limited to) magnesium or manganese or iron or cobalt or zinc aluminophosphate and silicoaluminophosphates, when aluminum is effectively replaced by Mg, Mn, Fe, Co or Zn. Different magnesium, manganese, iron, cobalt and zinc compounds and their mixtures are suitable for use as the magnesium, manganese, iron, cobalt and zinc component in the present invention. The magnesium, manganese, iron, cobalt and zinc compounds include, but are not limited to magnesium sulfate, magnesium fluoride, magnesium chloride, magnesium bromide, magnesium iodide, magnesium acetate, magnesium oxide, manganese(II) sulfate, manganese(II) fluoride, manganese(II) chloride, manganese(II) bromide, manganese(II) iodide, manganese(II) acetate, manganese(II) oxide, iron(II) oxalate, iron(II) chloride, iron(II) sulfate, iron(III) chloride, iron(III) nitrate, cobalt(II) sulfate, cobalt(II) fluoride, cobalt(II) chloride, cobalt(II) bromide, cobalt(II) iodide, cobalt(II) acetate, cobalt(II) oxide, zinc sulfate, zinc fluoride, zinc chloride, zinc bromide, zinc iodide, zinc acetate, zinc oxide.

In a third aspect of the invention, provided are compositions prepared for manufacturing a molecular sieve of the first aspect of the invention (STA-18C). The composition can have a molar compositional ratio of:

| | |
|---|---|
| P/A | 0.5-0.99 |
| MeO$_2$/A | 0.02-1.0 |
| SDA1 (1,4-diazabicyclo[2.2.2]octane derivative)/A | 0.1-0.6 |
| SDA2 (lower alkyl amine)/A | 0.1-0.6 |
| Lower alkyl ammonia hydroxide/A | 0.1-0.6 |
| H$_2$O/A | 20-200 | where P the source of phosphorous and is calculated as being in the oxide form ($P_2O_5$), A is Al, Fe, Cr, B, Ga or combinations thereof and is calculated as being in the oxide form ($A_2O_3$); and Me is Si, Ge, Mg or combinations thereof and is calculated as being in the oxide form ($MO_2$).

The molar ratio of P to A can be in the range of from about 0.5 to about 0.99, preferably from about 0.55 to about 0.75, more preferably from about 0.68 to about 0.71, where the endpoints can be included.

The molar ratio of MeO$_2$ to A can be in the range of from about 0.02 to about 1.0, preferably from about 0.01 to about 1.0, more preferably from about 0.5 to about 0.9, even more preferably from about 0.58 to about 0.75, where the endpoints can be included.

The molar ratio of STA1, a 1,4-diazabicyclo [2.2.2]octane derivative to A can be in the range of from about 0.1 to about 0.60, preferably from about 0.20 to about 0.3, where the endpoints can be included.

The molar ratio of STA2, a lower alkyl amine to A can be in the range of from about 0.1 to about 0.60, preferably from about 0.20 to about 0.3, where the endpoints can be included.

The molar ratio of a lower alkyl ammonium hydroxide to A can be in the range of from about 0.1 to about 0.60, preferably from about 0.20 to about 0.3, where the endpoints can be included.

The molar ratio of water to A can be in the range of from about 20 to about 200, preferably from about 60 to about 120, more preferably about 70 to about 90, where the endpoints can be included.

It is preferable that the pH value of the final reaction mixture be in the range from about 5.5 to about 8.5, preferably from about 6.5 to about 7.5, where the endpoints can be included. The pH value of a mixture can be adjusted, if desired, by adding an appropriate amount of a base such as a lower alkyl amine like tetrabutylammonium hydroxide.

When STA-18 to be produced comprises a SAPO, the composition comprises a silica component, a phosphorus component, an aluminum component, structure directing agents (SDAs) and a lower alkyl ammonia hydroxide. These components are present in a mixture described by the general formula as follows:

A SiO$_2$:1Al(OH)$_3$:B H$_3$PO$_4$:C H$_2$O:D(SDA1)1,4-
diazabicyclo[2.2.2]octane derivative:E(SDA2)
lower alkyl amine:F lower alkyl ammonium
hydroxide The molar ratio of silicon to aluminum hydroxide can be in the range of from about 0.01 to about 0.50, preferably from about 0.25 to about 0.45, more preferably from about 0.29 to about 0.32, where the endpoints can be included.

The molar ratio of aluminum hydroxide to H$_3$PO$_4$ can be in the range of from about 0.5 to about 0.99, preferably from about 0.55 to about 0.75, more preferably from about 0.68 to about 0.71, where the endpoints can be included.

The molar ratio of aluminum hydroxide to water can be in the range of from about 10 to about 100, preferably from about 30 to about 60, more preferably about 35 to about 45, where the endpoints can be included.

The molar ratio of aluminum hydroxide to SDA1 (1,4-diazabicyclo[2.2.2]octane derivative) can be in the range of from about 0.05 to about 0.30, preferably from about 0.10 to about 0.15, where the endpoints can be included.

The molar ratio of aluminum hydroxide to SDA2 (lower alkyl amine) can be in the range of from about 0.05 to about 0.5, preferably from about 0.1 to about 0.2, more preferably about 0.12 to about 0.15, where the endpoints can be included.

The molar ratio of aluminum hydroxide to the lower alkyl ammonium hydroxide can be in the range of from about 0.05 to about 0.5, preferably from about 0.15 to about 0.35, more preferably from about 0.25 to about 0.3, where the endpoints can be included.

It is preferable that the pH value of the final reaction mixture be in the range from about 5.5 to about 8.5, preferably from about 6.5 to about 7.5, where the endpoints can be included. The pH value of a mixture can be adjusted, if desired, by adding an appropriate amount of a base, preferably a lower alkyl ammonium hydroxide, such as tetrabutylammonium hydroxide.

When STA-18 comprises an MeAPO, the composition comprises a phosphorus component, an aluminum component, one metal cation of valence +2 selected from the group consisting of Mg$^{2+}$, Zn$^{2+}$, Co$^{2+}$, Mn$^{2+}$, Fe$^{2+}$, a structure directing agents (SDAs) and a lower alkyl ammonia hydroxide. These components are present in a mixture described by the general formula as follows:

A M$^{2+}$O$_2$:1 Al(OH)$_3$:B H$_3$PO$_4$:C H$_2$O:D (SDA1)1,4-
diazabicyclo[2.2.2]octane derivative:E (SDA2)
lower alkyl amine:F lower alkyl ammonium
hydroxide The molar ratio of $M^{2+}O_2$ to aluminum hydroxide can be in the range of from about 0.01 to about 0.50.

The molar ratio of aluminum hydroxide to $H_3PO_4$ can be in the range of from about 0.5 to about 0.99.

The molar ratio of aluminum hydroxide to water can be in the range of from about 10 to about 100.

The molar ratio of aluminum hydroxide to SDA1 (1,4-diazabicyclo[2.2.2]octane derivative) can be in the range of from about 0.05 to about 0.30.

The molar ratio of aluminum hydroxide to SDA2 (lower alkyl amine) can be in the range of from about 0.05 to about 0.5.

The molar ratio of aluminum hydroxide to the lower alkyl ammonium hydroxide can be in the range of from about 0.05 to about 0.5.

It is preferable that the pH value of the final reaction mixture be in the range from about 5.5 to about 8.5, preferably from about 6.5 to about 7.5, where the endpoints can be included. The pH value of a mixture can be adjusted, if desired, by adding an appropriate amount of a base, preferably a lower alkyl ammonium hydroxide, such as tetrabutylammonium hydroxide.

In a fourth aspect of the invention, provided is catalytic composition comprising a calcined molecular sieve (STA-18C) of the first aspect of the invention. STA-18C, the zeolite formed by the calcination of STA-18AP, is useful as a catalyst in certain applications. The dried STA-18AP crystals are preferably calcined, but can also be used without calcination. STA-18C can be used either without a post-synthesis metal exchange or with a post-synthesis metal exchange, preferably with a post-synthesis metal exchange. Thus, in certain aspects of the invention, provided is a catalyst comprising STA-18C that is free or essentially free of any exchanged metal, particularly post-synthesis exchanged or impregnated metals. STA-18C preferably can comprise one or more catalytic metal ions exchanged or otherwise impregnated into the channels and/or cavities of the zeolite. Examples of metals that can be post-zeolite synthesis exchanged or impregnated include transition metals, including copper, nickel, zinc, iron, tungsten, molybdenum, cobalt, titanium, zirconium, manganese, chromium, vanadium, niobium, as well as tin, bismuth, and antimony; noble metals including platinum group metals (PGMs), such as ruthenium, rhodium, palladium, indium, platinum, and precious metals such as gold and silver; alkaline earth metals such as beryllium, magnesium, calcium, strontium, and barium; and rare earth metals such as lanthanum, cerium, praseodymium, neodymium, europium, terbium, erbium, ytterbium, and yttrium. Preferred transition metals for post-synthesis exchange are base metals, and preferred base metals include those selected from the group consisting of manganese, iron, cobalt, nickel, copper, noble metals including platinum group metals (PGMs) and mixtures thereof.

The transition metal can be present in an amount of about 0.1 to about 10 weight percent, for example about 0.1 to about 5 weigh percent, about 0.1 to about 1.0 weight percent, about 2.5 to about 3.5 weight percent, and about 4.5 to about 5.5 weight percent, wherein the weight percent is relative to the total weight of the zeolite material, and the endpoints can be included.

Particularly preferred exchanged metals include copper and iron, particularly when combined with calcium and/or cerium and particularly when the transition metals ($T_M$) and the alkaline metals ($A_M$) are present in a $T_M:A_M$ molar ratio of about 15:1 to about 1:1, for example about 10:1 to about 2:1, about 10:1 to about 3:1, or about 6:1 to about 4:1, where the endpoints can be included Metals incorporated post-synthesis can be added to the molecular sieve via any known technique such as ion exchange, impregnation, isomorphous substitution, etc.

These exchanged metal cations are distinct from metals constituting the molecular framework of the zeolite, and thus metal exchanged zeolites are distinct from metal-substituted zeolites.

Catalysts of the present invention are particularly applicable for heterogeneous catalytic reaction systems (i.e., solid catalyst in contact with a gas reactant). To improve contact surface area, mechanical stability, and/or fluid flow characteristics, the catalysts can be disposed on and/or within a substrate, preferably a porous substrate. A washcoat containing the catalyst can be applied to an inert substrate, such as corrugated metal plate or a honeycomb cordierite brick. Alternatively, the catalyst is kneaded along with other components such as fillers, binders, and reinforcing agents, into an extrudable paste which then can be extruded through a die to form a honeycomb brick or extruded body such as a cylinder, trilobe or quadralobe. The catalyst may also be in the form of a micro-spherical particle (10-150 microns in diameter) containing the SAPO-56 of the present invention together with fillers, binders and/or reinforcing agents. The micro-spherical particle can be prepared by spray drying or other suitable techniques. Accordingly, a catalyst article can comprise an STA-18 molecular sieve described herein coated on and/or incorporated into a substrate.

Certain aspects of the invention provide a catalytic washcoat. The washcoat comprising a STA-18C described herein is preferably a solution, suspension, or slurry. Suitable coatings include surface coatings, coatings that penetrate a portion of the substrate, coatings that permeate the substrate, or some combination thereof.

A washcoat can also include non-catalytic components, such as fillers, binders, stabilizers, rheology modifiers, and other additives, including one or more of alumina, silica, non-zeolite silica alumina, titania, zirconia, ceria. Where the catalyst is part of a washcoat composition, the washcoat can further comprise a binder containing Ce or ceria. When the binder contains Ce or ceria, the Ce containing particles in the binder are significantly larger than the Ce containing particles in the catalyst. The catalyst composition can comprise pore-forming agents such as graphite, cellulose, starch, polyacrylate, and polyethylene, and the like. These additional components do not necessarily catalyze the desired reaction, but instead improve the catalytic material's effectiveness, for example, by increasing its operating temperature range, increasing contact surface area of the catalyst, increasing adherence of the catalyst to a substrate, etc. The washcoat loading on, or in, the substrate can be between about 0.3 $g/in^3$ to about 3.5 $g/in^3$, where the endpoints can be included. The loading can be a function of the type of substrate used and the backpressure that results from the loading on a specific type of substrate. The lower limit for the washcoat loading can be 0.5 $g/in^3$, 0.8 $g/in^3$, 1.0 $g/in^3$, 1.25 $g/in^3$, or 1.5 $g/in^3$. The upper limit for the washcoat loading can be 3.5 $g/in^3$, 3.25 $g/in^3$, 3.0 $g/in^3$, 2.75 $g/in^3$, 2.5 $g/in^3$, 2.25 $g/in^3$, 2.0 $g/in^3$, 1.75 $g/in^3$ or 1.5 $g/in^3$.

Two of the most common substrate designs to which catalyst can be applied are plate and honeycomb. Preferred substrates, particularly for mobile applications, include flow-through monoliths having a so-called honeycomb geometry that comprise multiple adjacent, parallel channels that are open on both ends and generally extend from the inlet face to the outlet face of the substrate and result in a high-surface area-to-volume ratio. For certain applications, the honeycomb flow-through monolith preferably has a high cell density, for example about 600 to 800 cells per square inch, and/or an average internal wall thickness of about 0.18-0.35 mm, preferably about 0.20-0.25 mm. For certain other applications, the honeycomb flow-through monolith preferably has a low cell density of about 150-600 cells per square inch, more preferably about 200-400 cells per square inch. Preferably, the honeycomb monoliths are porous. In addition to cordierite, silicon carbide, silicon nitride, ceramic, and metal, other materials that can be used for the substrate include aluminum nitride, silicon nitride, aluminum titanate, α-alumina, mullite, e.g., acicular mullite, pollucite, a thermet such as $Al_2OsZFe$, $Al_2O_3$/Ni or $B_4CZFe$, or composites comprising segments of any two or more thereof. Preferred materials include cordierite, silicon carbide, and alumina titanate.

Plate-type catalysts have lower pressure drops and are less susceptible to plugging and fouling than the honeycomb types, which is advantageous in high efficiency stationary applications, but plate configurations can be much larger and more expensive. A honeycomb configuration is typically smaller than a plate type, which is an advantage in mobile applications, but has higher pressure drops and plug more easily. The plate substrate can be constructed of metal, preferably corrugated metal.

A catalyst article can be made by a process described herein. The catalyst article can be produced by a process that includes the steps of applying a metal containing STA-18C, preferably as a washcoat, to a substrate as a layer either before or after at least one additional layer of another composition for treating exhaust gas has been applied to the substrate. The one or more catalyst layers on the substrate, including the layer comprising STA-18C, are arranged in consecutive layers. As used herein, the term "consecutive" with respect to catalyst layers on a substrate means that each layer is contact with its adjacent layer(s) and that the catalyst layers as a whole are arranged one on top of another on the substrate.

The STA-18C catalyst can be disposed on the substrate as a first layer or zone and another composition, such as an oxidation catalyst, reduction catalyst, scavenging component, or $NO_x$ storage component, can be disposed on the substrate as a second layer or zone. As used herein, the terms "first layer" and "second layer" are used to describe the relative positions of catalyst layers in the catalyst article with respect to the normal direction of exhaust gas flow-through, past, and/or over the catalyst article. Under normal exhaust gas flow conditions, exhaust gas contacts the first layer prior to contacting the second layer. The second layer can be applied to an inert substrate as a bottom layer and the first layer is a top layer that is applied over the second layer as a consecutive series of sub-layers.

The exhaust gas can penetrate (and hence contact) the first layer, before contacting the second layer, and subsequently returns through the first layer to exit the catalyst component.

The first layer can be a first zone disposed on an upstream portion of the substrate and the second layer is disposed on the substrate as a second zone, wherein the second zone is downstream of the first.

The catalyst article can be produced by a process that includes the steps of applying STA-18C, preferably as a washcoat, to a substrate as a first zone, and subsequently applying at least one additional composition for treating an exhaust gas to the substrate as a second zone, wherein at least a portion of the first zone is downstream of the second zone. Alternatively, a composition comprising STA-18C can be applied to the substrate in a second zone that is downstream of a first zone containing the additional composition.

Examples of additional compositions include oxidation catalysts, reduction catalysts, scavenging components (e.g., for sulfur, water, etc.), or $NO_x$ storage components.

To reduce the amount of space required for an exhaust system, individual exhaust components can be designed to perform more than one function. For example, applying an SCR catalyst to a wall-flow filter substrate instead of a flow-through substrate serves to reduce the overall size of an exhaust treatment system by allowing one substrate to serve two functions, namely catalytically reducing $NO_x$ concentration in the exhaust gas and mechanically removing soot from the exhaust gas. The substrate can be a honeycomb wall-flow filter or partial filter. Wall-flow filters are similar to flow-through honeycomb substrates in that they contain a plurality of adjacent, parallel channels. However, the channels of flow-through honeycomb substrates are open at both ends, whereas the channels of wall-flow substrates have one end capped, wherein the capping occurs on opposite ends of adjacent channels in an alternating pattern. Capping alternating ends of channels prevents the gas entering the inlet face of the substrate from flowing straight through the channel and existing. Instead, the exhaust gas enters the front of the substrate and travels into about half of the channels where it is forced through the channel walls prior to entering the second half of the channels and exiting the back face of the substrate.

The substrate wall has a porosity and pore size that is gas permeable, but traps a major portion of the particulate matter, such as soot, from the gas as the gas passes through the wall. Preferred wall-flow substrates are high efficiency filters. Wall flow filters for use with the present invention preferably have an efficiency of ≥70%, ≥about 75%, ≥about 80%, or ≥about 90%. The efficiency can be from about 75 to about 99%, about 75 to about 90%, about 80 to about 90%, or about 85 to about 95%. Here, efficiency is relative to soot and other similarly sized particles and to particulate concentrations typically found in conventional diesel exhaust gas. For example, particulates in diesel exhaust can range in size from 0.05 microns to 2.5 microns. Thus, the efficiency can be based on this range or a sub-range, such as 0.1 to 0.25 microns, 0.25 to 1.25 microns, or 1.25 to 2.5 microns.

Porosity is a measure of the percentage of void space in a porous substrate and is related to backpressure in an exhaust system: generally, the lower the porosity, the higher the backpressure. Preferably, the porous substrate has a porosity of about 30 to about 80%, for example about 40 to about 75%, about 40 to about 65%, or from about 50 to about 60%, where the endpoints can be included.

The pore interconnectivity, measured as a percentage of the substrate's total void volume, is the degree to which pores, void, and/or channels, are joined to form continuous paths through a porous substrate, i.e., from the inlet face to the outlet face. In contrast to pore interconnectivity is the sum of closed pore volume and the volume of pores that have a conduit to only one of the surfaces of the substrate. Preferably, the porous substrate has a pore interconnectivity volume of ≥about 30%, more preferably ≥about 40%.

The mean pore size of the porous substrate is also important for filtration. Mean pore size can be determined by any acceptable means, including by mercury porosimetry. The mean pore size of the porous substrate should be of a high enough value to promote low backpressure, while providing an adequate efficiency by either the substrate per se, by promotion of a soot cake layer on the surface of the substrate, or combination of both. Preferred porous substrates have a mean pore size of about 10 to about 40 μm, for example about 20 to about 30 μm, about 10 to about 25 μm, about 10 to about 20 μm, about 20 to about 25 μm, about 10 to about 15 μm, and about 15 to about 20 μm.

In general, the production of an extruded solid body, such as honeycomb flow-through or wall-flow filter, containing the catalyst STA-18C involves blending STA-18C, a binder, an optional organic viscosity-enhancing compound into an homogeneous paste which is then added to a binder/matrix component or a precursor thereof and optionally one or more of stabilized ceria, and inorganic fibers. The blend is compacted in a mixing or kneading apparatus or an extruder. The mixtures have organic additives such as binders, pore formers, plasticizers, surfactants, lubricants, dispersants as processing aids to enhance wetting and therefore produce a uniform batch. The resulting plastic material is then molded, in particular using an extrusion press or an extruder including an extrusion die, and the resulting moldings are dried and calcined. The organic additives are "burnt out" during calcinations of the extruded solid body. STA-18C, the catalytically active calcined product, can also be washcoated or otherwise applied to the extruded solid body as one or more sub-layers that reside on the surface or penetrate wholly or partly into the extruded solid body.

The binder/matrix component is preferably selected from the group consisting of cordierite, nitrides, carbides, borides, intermetallics, lithium aluminosilicate, a spinel, an optionally doped alumina, a silica source, titania, zirconia, titania-zirconia, zircon and mixtures of any two or more thereof. The paste can optionally contain reinforcing inorganic fibers selected from the group consisting of carbon fibers, glass fibers, metal fibers, boron fibers, alumina fibers, silica fibers, silica-alumina fibers, silicon carbide fibers, potassium titanate fibers, aluminum borate fibers and ceramic fibers.

The alumina binder/matrix component is preferably gamma alumina, but can be any other transition alumina, i.e., alpha alumina, beta alumina, chi alumina, eta alumina, rho alumina, kappa alumina, theta alumina, delta alumina, lanthanum beta alumina and mixtures of any two or more such transition aluminas. It is preferred that the alumina is doped with at least one non-aluminum element to increase the thermal stability of the alumina. Suitable alumina dopants include silicon, zirconium, barium, lanthanides and mixtures of any two or more thereof. Suitable lanthanide dopants include La, Ce, Nd, Pr, Gd and mixtures of any two or more thereof.

Preferably, STA-18C, the calcined product, is dispersed throughout, and preferably evenly throughout, the entire extruded catalyst body.

Where any of the above extruded solid bodies are made into a wall-flow filter, the porosity of the wall-flow filter can be from 30-80%, such as from 40-70%. Porosity and pore volume and pore radius can be measured e.g. using mercury intrusion porosimetry.

In a fifth aspect of the invention, provided is a method for treating an exhaust gas from an engine by contacting the exhaust gas with a calcined molecular sieve of the first aspect of the invention. The method can be used for the reduction of $NO_x$ compounds and/or oxidation of $NH_3$ in a gas, which comprises contacting the gas with STA-18C or a metal containing STA-18C for a time sufficient to reduce the level of $NO_x$ compounds in the gas.

STA-18C or a metal containing STA-18C can promote the reaction of a reductant, preferably ammonia, with nitrogen oxides to selectively form elemental nitrogen ($N_2$) and water ($H_2O$). Thus, the catalyst can be formulated to favor the reduction of nitrogen oxides with a reductant (i.e., an SCR catalyst). Examples of such reductants include hydrocarbons (e.g., C3-C6 hydrocarbons) and nitrogenous reductants such as ammonia and ammonia hydrazine or any suitable ammonia precursor, such as urea ($(NH_2)_2CO$), ammonium carbonate, ammonium carbamate, ammonium hydrogen carbonate or ammonium formate.

STA-18C, or a metal containing STA-18C, can also promote the oxidation of ammonia. Preferably, STA-18C contains one or more metal ions, such as copper or iron, that are impregnated into STA-18C. The catalyst can be formulated to favor the oxidation of ammonia with oxygen, particularly a concentrations of ammonia typically encountered downstream of an SCR catalyst (e.g., ammonia oxidation (AMOX) catalyst, such as an ammonia slip catalyst (ASC)). STA-18C, or a metal containing STA-18C, can be disposed as a top layer over an oxidative under-layer, wherein the under-layer comprises a platinum group metal (PGM) catalyst or a non-PGM catalyst. Preferably, the catalyst component in the underlayer is disposed on a high surface area support, including but not limited to alumina.

SCR and AMOX operations can be performed in series, wherein both processes utilize a catalyst comprising STA-18C, or a metal containing STA-18C, described herein, and wherein the SCR process occurs upstream of the AMOX process. For example, an SCR formulation of the catalyst can be disposed on the inlet side of a filter and an AMOX formulation of the catalyst can be disposed on the outlet side of the filter.

Accordingly, provided is a method for the reduction of $NO_x$ compounds or oxidation of $NH_3$ in a gas, which comprises contacting the gas with a catalyst composition described herein for the catalytic reduction of $NO_x$ compounds for a time sufficient to reduce the level of $NO_x$ compounds and/or $NH_3$ in the gas. A catalyst article can have an ammonia slip catalyst disposed downstream of a selective catalytic reduction (SCR) catalyst. The ammonia slip catalyst can oxidize at least a portion of any nitrogenous reductant that is not consumed by the selective catalytic reduction process. The ammonia slip catalyst can be disposed on the outlet side of a wall flow filter and an SCR catalyst can be disposed on the upstream side of a filter. The ammonia slip catalyst can be disposed on the downstream end of a flow-through substrate and an SCR catalyst can be disposed on the upstream end of the flow-through substrate. The ammonia slip catalyst and SCR catalyst can be disposed on separate bricks within the exhaust system. These separate bricks can be adjacent to, and in contact with, each other or separated by a specific distance, provided that they are in fluid communication with each other and provided that the SCR catalyst brick is disposed upstream of the ammonia slip catalyst brick.

The SCR and/or AMOX process can be performed at a temperature of ≥100° C., preferably at a temperature from about 150° C. to about 750° C., more preferably from about 175 to about 550° C., even more preferably from 175 to 400° C.

In some conditions, the temperature range can be from 450 to 900° C., preferably 500 to 750° C., more preferably 500 to 650° C., even more preferably 450 to 550° C. Temperatures greater than 450° C. are particularly useful for treating exhaust gases from a heavy and light duty diesel engine that is equipped with an exhaust system comprising (optionally catalyzed) diesel particulate filters which are regenerated actively, e.g. by injecting hydrocarbon into the exhaust system upstream of the filter, wherein the zeolite catalyst for use in the present invention is located downstream of the filter.

Methods of the present invention can comprise one or more of the following steps: (a) accumulating and/or combusting soot that is in contact with the inlet of a catalytic filter; (b) introducing a nitrogenous reducing agent into the exhaust gas stream prior to contacting the catalytic filter, preferably with no intervening catalytic steps involving the treatment of $NO_x$ and the reductant; (c) generating $NH_3$ over a $NO_x$ adsorber catalyst or lean $NO_x$ trap, and preferably using such $NH_3$ as a reductant in a downstream SCR reaction; (d) contacting the exhaust gas stream with a DOC to oxidize hydrocarbon based soluble organic fraction (SOF) and/or carbon monoxide into $CO_2$, and/or oxidize NO into $NO_2$, which in turn, can be used to oxidize particulate matter in particulate filter; and/or reduce the particulate matter (PM) in the exhaust gas; (e) contacting the exhaust gas with one or more flow-through SCR catalyst device(s) in the presence of a reducing agent to reduce the $NO_x$ concentration in the exhaust gas; and (f) contacting the exhaust gas with an ammonia slip catalyst, preferably downstream of the SCR catalyst to oxidize most, if not all, of the ammonia prior to emitting the exhaust gas into the atmosphere or passing the exhaust gas through a recirculation loop prior to exhaust gas entering/re-entering the engine.

All, or at least a portion of, the nitrogen-based reductant, particularly $NH_3$, for consumption in the SCR process can be supplied by a $NO_x$ adsorber catalyst (NAC), a lean $NO_x$ trap (LNT), or a $NO_x$ storage/reduction catalyst (NSRC), disposed upstream of the SCR catalyst, e.g., a SCR catalyst of the present invention disposed on a wall-flow filter. NAC components useful in the present invention include a catalyst combination of a basic material (such as alkali metal, alkaline earth metal or a rare earth metal, including oxides of alkali metals, oxides of alkaline earth metals, and combinations thereof), and a precious metal (such as platinum), and optionally a reduction catalyst component, such as rhodium. Specific types of basic material useful in the NAC include cesium oxide, potassium oxide, magnesium oxide, sodium oxide, calcium oxide, strontium oxide, barium oxide, and combinations thereof. The precious metal is preferably present at about 10 to about 200 $g/ft^3$, such as 20 to 60 $g/ft^3$. Alternatively, the precious metal of the catalyst is characterized by the average concentration which can be from about 40 to about 100 $grams/ft^3$.

During periodically rich regeneration events, $NH_3$ can be generated over a $NO_x$ adsorber catalyst. The SCR catalyst downstream of the $NO_x$ adsorber catalyst can improve the overall system $NO_x$ reduction efficiency. In the combined system, the SCR catalyst is capable of storing the released $NH_3$ from the NAC catalyst during rich regeneration events and utilizes the stored $NH_3$ to selectively reduce some or all of the $NO_x$ that slips through the NAC catalyst during the normal lean operation conditions.

The method for treating exhaust gas as described herein can be performed on an exhaust gas derived from a combustion process, such as from an internal combustion engine (whether mobile or stationary), a gas turbine and coal or oil fired power plants. The method can also be used to treat gas from industrial processes such as refining, from refinery heaters and boilers, furnaces, the chemical processing industry, coke ovens, municipal waste plants and incinerators, etc. The method can be used for treating exhaust gas from a vehicular lean burn internal combustion engine, such as a diesel engine, a lean-burn gasoline engine or an engine powered by liquid petroleum gas or natural gas.

In certain aspects, the invention is a system for treating exhaust gas generated by combustion process, such as from an internal combustion engine (whether mobile or stationary), a gas turbine, coal or oil fired power plants, and the like. Such systems include a catalytic article comprising STA-18C, described herein, and at least one additional component for treating the exhaust gas, wherein the catalytic article and at least one additional component are designed to function as a coherent unit.

A system can comprise a catalytic article comprising STA-18C or a metal containing STA-18C, a conduit for directing a flowing exhaust gas, and a source of nitrogenous reductant disposed upstream of the catalytic article. The system can include a controller for metering the nitrogenous reductant into the flowing exhaust gas only when it is determined that STA-18C or a metal containing STA-18C is capable of catalyzing $NO_x$ reduction at or above a desired efficiency over a specific temperature range, such as at above 100° C., above 150° C. or above 175° C. The metering of the nitrogenous reductant can be arranged such that 60% to 200% of theoretical ammonia is present in exhaust gas entering the SCR catalyst calculated at 1:1 $NH_3/NO$ and 4:3 $NH_3/NO_2$.

The system can comprise an oxidation catalyst (e.g., a diesel oxidation catalyst (DOC)) for oxidizing nitrogen monoxide in the exhaust gas to nitrogen dioxide can be located upstream of a point of metering the nitrogenous reductant into the exhaust gas. The oxidation catalyst can be adapted to yield a gas stream entering the SCR zeolite catalyst having a ratio of NO to $NO_2$ of from about 4:1 to about 1:3 by volume, e.g. at an exhaust gas temperature at oxidation catalyst inlet of 250° C. to 450° C. The oxidation catalyst can include at least one platinum group metal (or some combination of these), such as platinum, palladium, or rhodium, coated on a flow-through monolith substrate. The at least one platinum group metal can be platinum, palladium or a combination of both platinum and palladium. The platinum group metal can be supported on a high surface area washcoat component such as alumina, a zeolite such as an aluminosilicate zeolite, silica, non-zeolite silica alumina, ceria, zirconia, titania or a mixed or composite oxide containing both ceria and zirconia.

A suitable filter substrate can be located between the oxidation catalyst and the SCR catalyst. Filter substrates can be selected from any of those mentioned above, e.g. wall flow filters. Where the filter is catalyzed, e.g. with an oxidation catalyst of the kind discussed above, preferably the point of metering nitrogenous reductant is located between the filter and the zeolite catalyst. Alternatively, if the filter is un-catalyzed, the means for metering nitrogenous reductant can be located between the oxidation catalyst and the filter.

A method for treating an exhaust gas comprises contacting a combustion exhaust gas containing $NO_x$ with a passive $NO_x$ absorber comprising a molecular sieve of the first aspect of the invention. A passive $NO_x$ absorber effective to adsorb $NO_x$ at or below a low temperature and release the adsorbed $NO_x$ at temperatures above the low temperature can comprise a noble metal and STA-18C. The noble metal can be selected from the group consisting of platinum, palladium, rhodium, gold, silver, iridium, ruthenium, osmium, and mixtures thereof, and is preferably palladium.

The passive $NO_x$ adsorber can be effective to adsorb $NO_x$ at, or below, a low temperature (preferably less than 250° C., more preferably about 200° C.) and release the adsorbed $NO_x$ at temperatures above the low temperature. The passive $NO_x$ adsorber comprises a noble metal and STA-18C. The noble metal is selected from the group consisting of palladium, platinum, rhodium, gold, silver, iridium, ruthenium, osmium, or mixtures thereof; more preferably, palladium, platinum, rhodium, or mixtures thereof. Palladium is particularly preferred.

The passive $NO_x$ adsorber can be prepared by any known means. For instance, the noble metal can be added to STA-18C to form the passive $NO_x$ adsorber by any known means, the manner of addition is not considered to be particularly critical. For example, a noble metal compound (such as palladium nitrate) can be supported on STA-18C by impregnation, adsorption, ion-exchange, incipient wetness, precipitation, or the like. Other metals can also be added to the passive $NO_x$ adsorber. Preferably, some of the noble metal (more than 1 percent of the total noble metal added) in the passive $NO_x$ adsorber is located inside the pores of STA-18C. More preferably, more than 5 percent of the total amount of noble metal is located inside the pores of STA-18C; and even more preferably can be greater than 10 percent or greater than 25% or greater than 50 percent of the total amount of noble metal that is located inside the pores of STA-18C.

Preferably, the passive $NO_x$ adsorber further comprises a flow-through substrate or filter substrate. The passive $NO_x$ adsorber can be coated onto the flow-through or filter substrate, and preferably deposited on the flow-through or filter substrate using a washcoat procedure to produce a passive $NO_x$ adsorber system.

The flow-through or filter substrate can be a substrate that is capable of containing catalyst components. The substrate is preferably a ceramic substrate or a metallic substrate. The ceramic substrate can be made of any suitable refractory material, e.g., alumina, silica, titania, ceria, zirconia, magnesia, zeolites, silicon nitride, silicon carbide, zirconium silicates, magnesium silicates, aluminosilicates, metallo aluminosilicates (such as cordierite and spudomene), or a mixture or mixed oxide of any two or more thereof. Cordierite, a magnesium aluminosilicate, and silicon carbide are particularly preferred.

The metallic substrates can be made of any suitable metal, and in particular heat-resistant metals and metal alloys such as titanium and stainless steel as well as ferritic alloys containing iron, nickel, chromium, and/or aluminum in addition to other trace metals.

The flow-through substrate is preferably a flow-through monolith having a honeycomb structure with many small, parallel thin-walled channels running axially through the substrate and extending throughout from an inlet or an outlet of the substrate. The channel cross-section of the substrate can be any shape, but is preferably square, sinusoidal, triangular, rectangular, hexagonal, trapezoidal, circular, or oval.

The filter substrate is preferably a wall-flow monolith filter. The channels of a wall-flow filter are alternately blocked, which allow the exhaust gas stream to enter a channel from the inlet, then flow through the channel walls, and exit the filter from a different channel leading to the outlet. Particulates in the exhaust gas stream are thus trapped in the filter.

The passive $NO_x$ adsorber can be added to the flow-through or filter substrate by any known means. A representative process for preparing the passive $NO_x$ adsorber using a washcoat procedure is set forth below. It will be understood that the process below can be varied according to different embodiments of the invention.

The pre-formed passive $NO_x$ adsorber can be added to the flow-through or filter substrate by a washcoating step. Alternatively, the passive $NO_x$ adsorber can be formed on the flow-through or filter substrate by first washcoating unmodified small pore molecular sieve onto the substrate to produce a molecular sieve-coated substrate. Noble metal can then be added to the STA-18C-coated substrate, which can be accomplished by an impregnation procedure, or the like.

The washcoating procedure is preferably performed by first slurrying finely divided particles of the passive $NO_x$ adsorber (or unmodified small pore molecular sieve) in an appropriate solvent, preferably water, to form the slurry. Additional components, such as transition metal oxides, binders, stabilizers, or promoters can also be incorporated in the slurry as a mixture of water soluble or water-dispersible compounds. The slurry preferably contains between 10 to 70 weight percent solids, more preferably between 20 to 50 weight percent. Prior to forming the slurry, the passive $NO_x$ adsorber (or unmodified small pore molecular sieve) particles are preferably subject to a size reduction treatment (e.g., milling) such that the average particle size of the solid particles is less than 20 microns in diameter.

The flow-through or filter substrate can then be dipped one or more times into the slurry or the slurry can be coated on the substrate such that there will be deposited on the substrate the desired loading of catalytic materials. If noble metal is not incorporated into STA-18C prior to washcoating the flow-through or filter substrate, the STA-18C-coated substrate is typically dried and calcined and then, the noble metal can be added to the molecular sieve-coated substrate by any known means, including impregnation, adsorption, or ion-exchange, for example, with a noble metal compound (such as palladium nitrate). Preferably, the entire length of the flow-through or filter substrate is coated with the slurry so that a washcoat of the passive $NO_x$ adsorber covers the entire surface of the substrate.

After the flow-through or filter substrate has been coated with the passive $NO_x$ adsorber, and impregnated with noble metal if necessary, the coated substrate is preferably dried and then calcined by heating at an elevated temperature to form the passive $NO_x$ adsorber-coated substrate. Preferably, the calcination occurs at 400 to 600° C. for approximately 1 to 8 hours.

The flow-through or filter substrate can be comprised of the passive $NO_x$ adsorber. In this case, the passive $NO_x$ adsorber can be extruded to form the flow-through or filter substrate. The passive $NO_x$ adsorber extruded substrate is preferably a honeycomb flow-through monolith.

Extruded molecular sieve substrates and honeycomb bodies, and processes for making them, are known in the art. See, for example, U.S. Pat. Nos. 5,492,883, 5,565,394, and 5,633,217 and U.S. Pat. No. Re. 34,804. Typically, the molecular sieve material is mixed with a permanent binder such as silicone resin and a temporary binder such as methylcellulose, and the mixture is extruded to form a green honeycomb body, which is then calcined and sintered to form the final small pore molecular sieve flow-through monolith. The molecular sieve can contain the noble metal prior to extruding such that a passive $NO_x$ adsorber monolith is produced by the extrusion procedure. Alternatively, the noble metal can be added to a pre-formed molecular sieve monolith in order to produce the passive $NO_x$ adsorber monolith.

The invention also includes an exhaust system for internal combustion engines comprising the passive $NO_x$ adsorber. The exhaust system preferably comprises one or more additional after-treatment devices capable of removing pollutants from internal combustion engine exhaust gases at normal operating temperatures. Preferably, the exhaust system comprises the passive $NO_x$ adsorber and one or more other catalyst components selected from: (1) a selective catalytic reduction (SCR) catalyst, (2) a particulate filter, (3) a SCR filter, (4) a $NO_x$ adsorber catalyst, (5) a three-way catalyst, (6) an oxidation catalyst, or any combination thereof. The passive $NO_x$ adsorber is preferably a separate component from any of the above after-treatment devices. Alternatively, the passive $NO_x$ adsorber can be incorporated as a component into any of the above after-treatment devices.

These after-treatment devices are well known in the art. Selective catalytic reduction (SCR) catalysts are catalysts that reduce $NO_x$ to $N_2$ by reaction with nitrogen compounds (such as ammonia or urea) or hydrocarbons (lean $NO_x$ reduction). A typical SCR catalyst is comprised of a vanadia-titania catalyst, a vanadia-tungsta-titania catalyst, or a metal/zeolite catalyst such as iron/beta zeolite, copper/beta zeolite, copper/SSZ-13, copper/SAPO-34, Fe/ZSM-5, or copper/ZSM-5.

Particulate filters are devices that reduce particulates from the exhaust of internal combustion engines. Particulate filters include catalyzed particulate filters and bare (non-catalyzed) particulate filters. Catalyzed particulate filters (for diesel and gasoline applications) include metal and metal oxide components (such as Pt, Pd, Fe, Mn, Cu, and ceria) to oxidize hydrocarbons and carbon monoxide in addition to destroying soot trapped by the filter.

Selective catalytic reduction filters (SCRF) are single-substrate devices that combine the functionality of an SCR and a particulate filter. They are used to reduce $NO_x$ and particulate emissions from internal combustion engines. In addition to the SCR catalyst coating, the particulate filter can also include other metal and metal oxide components (such as Pt, Pd, Fe, Mn, Cu, and ceria) to oxidize hydrocarbons and carbon monoxide in addition to destroying soot trapped by the filter. $NO_x$ adsorber catalysts (NACs) are designed to adsorb $NO_x$ under lean exhaust conditions, release the adsorbed $NO_x$ under rich conditions, and reduce the released $NO_x$ to form Nz. NACs typically include a $NO_x$-storage component (e.g., Ba, Ca, Sr, Mg, K, Na, Li, Cs, La, Y, Pr, and Nd), an oxidation component (preferably Pt) and a reduction component (preferably Rh). These components are contained on one or more supports.

Three-way catalysts (TWCs) are typically used in gasoline engines under stoichiometric conditions in order to convert $NO_x$ to Nz, carbon monoxide to $CO_2$, and hydrocarbons to $CO_2$ and $H_2O$ on a single device.

Oxidation catalysts, and in particular diesel oxidation catalysts (DOCS), are well-known in the art. Oxidation catalysts are designed to oxidize CO to $CO_2$ and gas phase hydrocarbons (HC) and an organic fraction of diesel particulates (soluble organic fraction) to $CO_2$ and $H_2O$. Typical oxidation catalysts include platinum and optionally also palladium on a high surface area inorganic oxide support, such as alumina, silica-alumina and a zeolite.

The exhaust system can be configured so that the passive $NO_x$ adsorber is located close to the engine and the additional after-treatment device(s) are located downstream of the passive $NO_x$ adsorber. Thus, under normal operating conditions, engine exhaust gas first flows through the passive $NO_x$ adsorber prior to contacting the after-treatment device(s). Alternatively, the exhaust system can contain valves or other gas-directing means such that during the low temperature period (below a temperature ranging from about 150 to 220° C., preferably 200° C., about as measured at the after-treatment device(s)), the exhaust gas is directed to contact the after-treatment device(s) before flowing to the passive $NO_x$ adsorber. Once the after-treatment device(s) reaches the operating temperature (about 150 to 220° C., preferably 200° C., as measured at the after-treatment device(s)), the exhaust gas flow is then redirected to contact the passive $NO_x$ adsorber prior to contacting the after-treatment device(s). This ensures that the temperature of the passive $NO_x$ adsorber remains low for a longer period of time, and thus improves efficiency of the passive $NO_x$ adsorber, while simultaneously allowing the after-treatment device(s) to more quickly reach operating temperature. U.S. Pat. No. 5,656,244, the teachings of which are incorporated herein by reference, for example, teaches means for controlling the flow of the exhaust gas during cold-start and normal operating conditions.

The invention also includes a method for treating exhaust gas from an internal combustion engine. The method comprises adsorbing $NO_x$ onto the passive $NO_x$ adsorber at temperatures at or below 250° C., preferably below 200° C., thermally desorbing $NO_x$ from the passive $NO_x$ adsorber at a temperature above the above stated temperature, and catalytically removing the desorbed $NO_x$ on a catalyst component downstream of the passive $NO_x$ adsorber.

The catalyst component downstream of the passive $NO_x$ adsorber can be an SCR catalyst, a particulate filter, a SCR filter, a $NO_x$ adsorber catalyst, a three-way catalyst, an oxidation catalyst, or combinations thereof.

In a six aspect of the invention, provided is a method of converting an oxygenate, such as methanol, to an olefin (MTO) by contacting methanol with a calcined molecular sieve of the first aspect of the invention. The reaction process for the conversion of an oxygenate to olefin (OTO) is well known in the art. Specifically, in an OTO reaction process, an oxygenate contacts a molecular sieve catalyst composition under conditions effective to convert at least a portion of the oxygenate to light olefins. When methanol is the oxygenate, the process is generally referred to as a methanol to olefin (MTO) reaction process. Methanol is a particularly preferred oxygenate for the synthesis of ethylene and/or propylene.

A process for converting an oxygenate feed to a light olefin product comprises: a) providing an oxygenate feed comprising a majority of methanol; b) providing a catalyst composition comprising STA-18C and optionally a basic metal oxide co-catalyst; and c) contacting the oxygenate feed with the catalyst composition under conditions sufficient to convert at least a portion of the oxygenate feed to a light olefin product.

An oxygenate feedstock, particularly a mixed alcohol composition containing methanol and ethanol, is a useful feedstock for a variety of catalytic processes, particularly oxygenate to olefin (OTO) reaction processes, in which a catalyst composition, typically containing a primary oxide catalyst having at least two of Al, Si, and P (e.g., an aluminosilicate molecular sieve, preferably a high-silica aluminosilicate molecular sieve) and preferably a basic metal oxide co-catalyst, can be used to convert the oxygenate feedstock into a light olefin product, e.g., containing ethylene and/or propylene, preferably including ethylene. The olefins can then be recovered and used for further processing, e.g., in the manufacture of polyolefins such as polyethylene and/or polypropylene, olefin oligomers, olefin copolymers, mixtures thereof, and/or blends thereof.

One or more additional components can be included in the feedstock that is directed to the OTO reaction system. For example, a feedstock directed to the OTO reaction system can optionally contain, in addition to methanol and ethanol, one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to 50 carbon atoms, preferably from 1 to 20 carbon atoms, more preferably from 1 to 10 carbon atoms, most preferably from 1 to 4 carbon atoms.

Non-limiting examples of aliphatic-containing compounds include: alcohols such as methanol, ethanol, n-propanol, isopropanol, and the like, alkyl-mercaptans such as methyl mercaptan and ethyl mercaptan, alkyl-sulfides such as methyl sulfide, alkyl amines such as methyl amine, alkyl ethers such as DME, diethyl ether and methyl ethyl ether, alkyl-halides such as methyl chloride and ethyl chloride, alkyl ketones such as dimethyl ketone, alkyl-aldehydes such as formaldehyde and acetaldehyde, and various organic acids such as formic acid and acetic acid.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene. Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomers can include, but are not limited to, unsaturated monomers, diolefins having 4 to 18 carbon atoms, conjugated or non-conjugated dienes, polyenes, vinyl monomers, and cyclic olefins.

A catalyst article for converting a low molecular weight oxygen containing species to an olefin rich hydrocarbon stream can comprise an STA-18 molecular sieve, where the STA-18 is disposed on a support and/or within a structure.

A catalyst article for converting a low molecular weight oxygen containing species to an aromatic rich hydrocarbon stream can comprise an STA-18 molecular sieve, where the STA-18 is disposed on a support and/or within a structure.

The catalyst can be incorporated or mixed with other additive materials. Such an admixture is typically referred to as formulated catalyst or as catalyst composition. Preferably, the additive materials are substantially inert to conversion reactions involving dialkyl ethers (e.g., dimethyl ether) and/or alkanols (e.g., methanol, ethanol, and the like).

One or more other materials can be mixed with STA-18C, particularly a material that is resistant to the temperatures and other conditions employed in organic conversion processes. Such materials can include catalytically active and inactive materials and synthetic or naturally occurring zeolites, as well as inorganic materials such as clays, silica, and/or other metal oxides such as alumina. The latter may be either naturally occurring or in the form of gelatinous precipitates or gels including mixtures of silica and metal oxides. Use of a catalytically active material can tend to change the conversion and/or selectivity of the catalyst in the oxygenate conversion process. Inactive materials suitably can serve as diluents to control the amount of conversion in the process so that products can be obtained in an economic and orderly manner without employing other means for controlling the rate of reaction. These materials can be incorporated into naturally occurring clays, e.g., bentonite and kaolin, to improve the crush strength of the catalyst under commercial operating conditions. The materials (e.g., clays, oxides, etc.) can function as binders for the catalyst. It can be desirable to provide a catalyst having good crush strength, because, in commercial use, it can be desirable to prevent the catalyst from breaking down into powder-like materials.

Naturally occurring clays that can be employed can include, but are not limited to, the montmorillonite and kaolin family, which families include the subbentonites, and the kaolins commonly known as Dixie, McNamee, Georgia and Florida clays, or others in which the main mineral constituent includes halloysite, kaolinite, dickite, nacrite, or anauxite. Such clays can be used in the raw state as originally mined or initially subjected to calcination, acid treatment, or chemical modification. Other useful binders can include, but are not limited to, inorganic oxides such as silica, titania, beryllia, alumina, and mixtures thereof.

In addition to the foregoing materials, the STA-18C can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The relative proportions of STA-18C and an inorganic oxide matrix can vary widely. For example, a mixture can include a zeolite content ranging from about 1 to about 90 percent by weight and more usually, particularly when the composite is prepared in the form of beads, in the range from about 2 to about 80 weight percent of the composite.

The invention also relates to C2, C3, C4 and C5 products formed by OTO or MTO application using STA-18C as a catalyst or co-catalyst.

EXAMPLES

STA-18 was prepared using trimethylamine and 1,6-(1,4-diazabicyclo[2.2.2]octane)hexyl dibromide (diDABCO-C6) or 1,7-(1,4-diazabicyclo[2.2.2]octane)heptyl dibromide (diDABCO-C7) or 1,8-(1,4-diazabicyclo[2.2.2]octane)octyl dibromide (diDABCO-C8) as SDAs. Tetrabutylammonium hydroxide (TBAOH) was used as a pH modifier for the SAPO preparation.

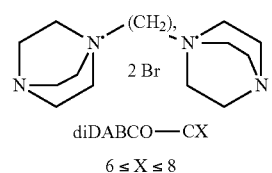

diDABCO—CX $6 \leq X \leq 8$

The following examples demonstrate, but do not limit, aspects of the present invention.

Structure-Directing Agents

The synthesis procedure for the preparation of the 3 SDAs in Examples 1-3 is reported in literature; Noble, G. W.; Wright, P. A.; Kvick, A. *J. Chem. Soc., Dalton. Trans.* 1997, 4485.

Example 1.
1,6-(1,4-diazabicyclo[2.2.2]octane)hexyl dibromide (diDABCO-C6)

13.0 g (0.05 mol) of 1,6-dibromohexane was dissolved in 50 mL ethanol and added droop-wise to a solution under stirring at 50° C. of 32.0 g (0.29 mol) of 1,4-diazabicyclo [2.2.2]octane (DABCO) dissolved in 100 mL ethanol. The mixture was refluxed for 24 hours. Once cold, the excess of ethanol was removed on a rotary evaporator leaving a white solid. That was washed with cold diethyl ether, acetonitrile and acetone and dried at 50° C. overnight. The reaction yields 24.60 g (yield 98%) of product which was analysed by NMR and elemental analysis.

Example 2. 1,7-(1,4-diazabicyclo[2.2.2]octane)heptyl dibromide (diDABCO-C7)

10.0 g (0.04 mol) of 1,7-dibromoheptane was dissolved in 50 mL ethanol and added droop-wise to a solution under stirring at 50° C. of 23.0 g (0.21 mol) of 1,4-diazabicyclo [2.2.2]octane (DABCO) dissolved in 100 mL ethanol. The mixture was refluxed for 24 hours. Once cold, the excess of ethanol was removed on a rotary evaporator leaving yellow oil. Subsequently cold diethyl ether was added to the oil to form a white solid precipitate that was washed with cold acetone and acetonitrile and then dried at 50° C. overnight. The reaction yielded 17.89 g (yield 96%) of product which was analysed by NMR and elemental analysis.

Example 3. 1,8-(1,4-diazabicyclo[2.2.2]octane)octyl dibromide (diDABCO-C8)

13.0 g (0.05 mol) of 1,8-dibromooctane was dissolved in 50 mL ethanol and added droop-wise to a solution under stirring at 50° C. of 28.4 g (0.25 mol) of 1,4-diazabicyclo [2.2.2]octane (DABCO) dissolved in 100 mL ethanol. The mixture was refluxed for 24 hours. Once cold, the excess of ethanol was removed on a rotary evaporator leaving yellow oil. Subsequently cold diethyl ether was added to the oil to form a white solid precipitate that was washed with cold acetone and acetonitrile and then dried at 50° C. overnight. The reaction yields 21.69 g (yield 91%) of product which was analysed by NMR and elemental analysis.

Example 4. Synthesis of STA-18 Using Trimethylamine and diDABCO-C6

A reaction gel having a molar composition:
0.3 $SiO_2$:1 $Al(OH)_3$:0.7$H_3PO_4$:40 $H_2O$:0.10 diDABCO-C6:0.13 trimethylamine:0.28 tetrabutylammonium hydroxide,
was prepared in 30 mL pressure vessel. The reagents used and order of addition was:
  a) The required amount of phosphoric acid ($H_3PO_4$ 85 wt. %, BDH) was weighted into a Teflon lined vessel.
  b) The required amount of silica (fumed silica powder 0.007 μm, Sigma Aldrich) and water were added to the phosphoric acid and stirred.
  c) The required amount of aluminium hydroxide (Al (OH)$_3$, Sigma Aldrich) was added to the above mixture.
  d) After stirring for 30 minutes, diDABCO-C6 (Example 1) was added.
  e) Trimethylamine (45 wt. %, Sigma Aldrich) was added over the above solution and the mixture was stirred for 10 minutes.
  f) Tetrabutylammonium hydroxide (40 wt. %, Sigma Aldrich) was finally added to the mixture.
In Examples 4, 6, 8 and 10, the pH of the gels were maintained at a pH of about 7 by the addition of tetrabuthylammonium hydroxide.
The final gel was stirred continuously at room temperature for at least 2 hours during the preparation procedure, until homogeneous, prior to being transferred to a Teflon-lined stainless steel autoclave and heated in static condition at 190° C. for 7 days. The resultant product was collected by filtration, washed with deionised $H_2O$, and dried in air at 80° C. for 12 hours.

The powder XRD pattern is shown in FIG. 1 and comprises the diffraction peaks in Table 5. Analysis by powder XRD indicated that the product was phase pure SFW.

TABLE 5

Diffraction peaks of as prepared material of Example 4.

| d-spacing [Å] | 2θ [°] | Rel. Int. [%] |
|---|---|---|
| 11.44 | 7.7 | 61 |
| 10.48 | 8.4 | 25 |
| 8.19 | 10.8 | 69 |
| 7.20 | 12.3 | 45 |
| 6.84 | 12.9 | 32 |
| 5.87 | 15.1 | 37 |
| 5.73 | 15.5 | 12 |
| 5.25 | 16.9 | 51 |
| 5.04 | 17.6 | 57 |
| 4.96 | 17.9 | 18 |
| 4.46 | 19.9 | 56 |
| 4.39 | 20.2 | 19 |
| 4.24 | 20.9 | 10 |
| 4.17 | 21.3 | 100 |
| 4.06 | 21.9 | 23 |
| 4.02 | 22.1 | 41 |
| 3.95 | 22.5 | 20 |
| 3.42 | 26.0 | 35 |
| 3.35 | 26.6 | 52 |
| 3.19 | 28.0 | 8 |
| 3.16 | 28.2 | 7 |
| 3.13 | 28.5 | 40 |
| 3.09 | 28.9 | 7 |
| 3.01 | 29.7 | 8 |
| 2.96 | 30.2 | 27 |
| 2.94 | 30.4 | 9 |
| 2.87 | 31.2 | 29 |
| 2.83 | 31.6 | 8 |
| 2.82 | 31.7 | 12 |
| 2.76 | 32.5 | 19 |
| 2.63 | 34.1 | 12 |
| 2.59 | 34.7 | 14 |

The crystal morphology of SAPO STA-18 synthesized with diDABCO-C6 and trimethylamine as SDAs was evaluated using a JEOL JSM 6010LA SEM. The crystals have a hexagonal prismatic morphology with side of length between 5-10 μm and about 2 μm thick. (FIGS. 2 and 3)

Figure 4:
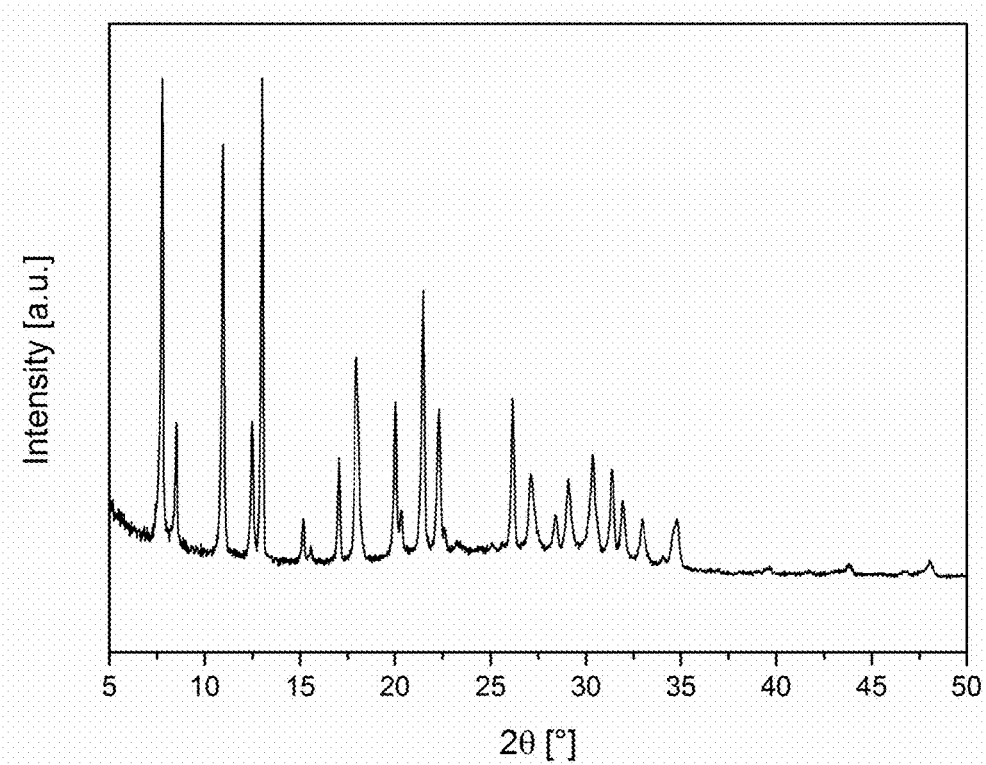
FIG. 4 is an XRD diffraction pattern of a sample of SAPO STA-18C as prepared in Example 5.

Example 5. Formation of STA-18C From SAPO STA-18 Synthesized with diDABCO-C6 and Trimethylamine as SDAs A portion of the as-made material from Example 4 was calcinated in dry oxygen. The material was heated at 600° C. and held at that temperature for 12 hours. The PXRD pattern of the calcined product and the list of diffraction peaks are shown in FIG. 4 and Table 6, respectively.

TABLE 6

Diffraction peaks of calcined material of Example 5.

| d-spacing [Å] | 2θ [°] | Rel. Int. [%] |
|---|---|---|
| 11.35 | 7.8 | 95 |
| 10.37 | 8.5 | 25 |
| 8.07 | 11.0 | 85 |
| 7.09 | 12.5 | 28 |
| 6.80 | 13.0 | 100 |

TABLE 6-continued

Diffraction peaks of calcined material of Example 5.

| d-spacing [Å] | 2θ [°] | Rel. Int. [%] |
|---|---|---|
| 5.84 | 15.2 | 9 |
| 5.20 | 17.0 | 21 |
| 4.94 | 17.9 | 39 |
| 4.43 | 20.0 | 32 |
| 4.36 | 20.3 | 9 |
| 4.14 | 21.5 | 54 |
| 3.98 | 22.3 | 29 |
| 3.41 | 26.2 | 31 |
| 3.29 | 27.1 | 16 |
| 3.14 | 28.4 | 8 |
| 3.07 | 29.0 | 16 |
| 2.94 | 30.4 | 21 |
| 2.85 | 31.4 | 19 |
| 2.80 | 31.9 | 13 |
| 2.72 | 33.0 | 9 |
| 2.58 | 34.8 | 9 |

Example 6. Synthesis of STA-18 Using Trimethylamine and diDABCO-C7

A reaction gel having a molar composition:
0.3 $SiO_2$:1 $Al(OH)_3$:0.7$H_3PO_4$:40 $H_2O$:0.10 diDABCO-C7:0.13 trimethylamine:0.28 tetrabutylammonium hydroxide, with 2 wt. % of SAPO-AFX seeds
was prepared in 30 mL pressure vessel. The reagents used and order of addition was:
  a) The required amount of phosphoric acid ($H_3PO_4$ 85 wt. %, BDH) was weighted into a Teflon lined vessel.
  b) The required amount of silica (fumed silica powder 0.007 μm, Sigma Aldrich) and water were added to the phosphoric acid and stirred.
  c) The required amount of aluminium hydroxide (Al(OH)$_3$, Sigma Aldrich) was added to the above mixture.
  d) After stirring for 30 minutes, diDABCO-C7 (Example 2) was added.
  e) Trimethylamine (45 wt. %, Sigma Aldrich) was added over the above solution and the mixture was stirred for 10 minutes.
  f) Tetrabutylammonium hydroxide (40 wt. %, Sigma Aldrich) was finally added to the mixture.
  g) 2 wt. % of SAPO-AFX seeds were finally added.

The final gel was stirred continuously at room temperature for at least 2 hours during the preparation procedure, until homogeneous, prior to being transferred to a Teflon-lined stainless steel autoclave and heated in static condition at 190° C. for 7 days. The resultant product was collected by filtration, washed with deionised $H_2O$, and dried in air at 80° C. for 12 hours.

The powder XRD pattern is shown in FIG. 5 and comprises the diffraction peaks in Table 7. Analysis by powder XRD indicated that the product was phase pure SFW.

TABLE 7

Diffraction peaks of as prepared material of Example 6.

| d-spacing [Å] | 2θ [°] | Rel. Int. [%] |
|---|---|---|
| 11.47 | 7.7 | 72 |
| 10.50 | 8.4 | 30 |
| 8.19 | 10.8 | 62 |
| 7.20 | 12.3 | 43 |
| 6.85 | 12.9 | 36 |
| 5.89 | 15.1 | 37 |
| 5.74 | 15.4 | 11 |
| 5.26 | 16.9 | 53 |
| 5.03 | 17.6 | 48 |
| 4.97 | 17.9 | 19 |
| 4.46 | 19.9 | 57 |
| 4.40 | 20.2 | 19 |
| 4.24 | 21.0 | 9 |
| 4.17 | 21.3 | 100 |
| 4.06 | 21.9 | 21 |
| 4.02 | 22.1 | 29 |
| 3.96 | 22.4 | 20 |
| 3.43 | 26.0 | 35 |
| 3.34 | 26.7 | 38 |
| 3.19 | 28.0 | 7 |
| 3.16 | 28.2 | 7 |
| 3.12 | 28.6 | 28 |
| 3.10 | 28.8 | 7 |
| 3.00 | 29.7 | 7 |
| 2.96 | 30.2 | 27 |
| 2.94 | 30.4 | 9 |
| 2.87 | 31.1 | 29 |
| 2.84 | 31.5 | 10 |
| 2.82 | 31.7 | 12 |
| 2.75 | 32.5 | 17 |
| 2.62 | 34.2 | 10 |
| 2.59 | 34.6 | 13 |

Example 7. Formation of STA-18C from SAPO STA-18 Synthesized with diDABCO-C7 and Trimethylamine as SDAs A portion of the as-made material from Example 7 was calcined in dry oxygen. The material was heated at 600° C. and held at that temperature for 12 hours.

Figure 6:
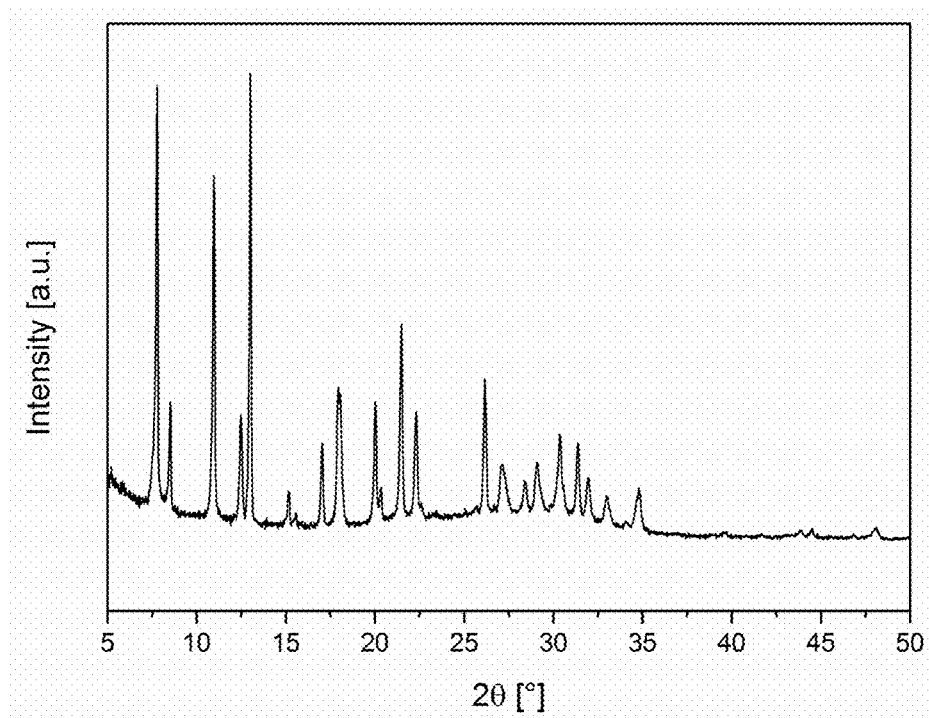
FIG. 6 is an XRD diffraction pattern of a sample of SAPO STA-18C as prepared in Example 7.

The PXRD pattern of the calcined product and the list of diffraction peaks are shown in FIG. 6 and Table 8, respectively.

TABLE 8

Diffraction peaks of calcined material of Example 7.

| d-spacing [Å] | 2θ [°] | Rel. Int. [%] |
|---|---|---|
| 11.35 | 7.8 | 96 |
| 10.38 | 8.5 | 25 |
| 8.06 | 11.0 | 78 |
| 7.08 | 12.5 | 23 |
| 6.80 | 13.0 | 100 |
| 5.84 | 15.2 | 8 |
| 5.20 | 17.1 | 20 |
| 4.94 | 17.9 | 31 |
| 4.43 | 20.0 | 27 |
| 4.36 | 20.3 | 7 |
| 4.13 | 21.5 | 43 |
| 3.98 | 22.3 | 24 |
| 3.41 | 26.2 | 31 |
| 3.29 | 27.1 | 12 |
| 3.14 | 28.4 | 8 |
| 3.07 | 29.1 | 13 |
| 2.95 | 30.3 | 20 |
| 2.85 | 31.4 | 18 |
| 2.80 | 32.0 | 10 |
| 2.71 | 33.0 | 6 |
| 2.58 | 35.0 | 9 |

Example 8. Synthesis of STA-18 Using Trimethylamine and diDABCO-C8)

A reaction gel having a molar composition:
0.3 SiO$_2$:1 Al(OH)$_3$:0.7H$_3$PO$_4$:40 H$_2$O:0.10 diDABCO-C8:0.11 trimethylamine:0.3 tetrabutylammonium hydroxide, with 2 wt. % of SAPO-AFX seeds
was prepared in 30 mL pressure vessel. The reagents used and order of addition was:
  a) The required amount of phosphoric acid (H$_3$PO$_4$ 85 wt. %, BDH) was weighted into a Teflon lined vessel.
  b) The required amount of silica (fumed silica powder 0.007 µm, Sigma Aldrich) and water were added to the phosphoric acid and stirred.
  c) The required amount of aluminium hydroxide (Al(OH)$_3$, Sigma Aldrich) was added to the above mixture.
  d) After stirring for 30 minutes, diDABCO-C8 (Example 3) was added.
  e) Trimethylamine (45 wt. %, Sigma Aldrich) was added over the above solution and the mixture was stirred for 10 minutes.
  f) Tetrabutylammonium hydroxide (40 wt. %, Sigma Aldrich) was finally added to the mixture.
  g) 2 wt. % of SAPO-AFX seeds were finally added.

The final gel was stirred continuously at room temperature for at least 2 hours during the preparation procedure, until homogeneous, prior to being transferred to a Teflon-lined stainless steel autoclave and heated in static condition at 190° C. for 7 days. The resultant product was collected by filtration, washed with deionised H$_2$O, and dried in air at 80° C. for 12 hours.

The powder XRD pattern is shown in FIG. 7 and comprises the diffraction peaks in Table 9. Analysis by powder XRD indicated that the product was phase pure SFW.

TABLE 9

Diffraction peaks of as prepared material of Example 8.

| d-spacing [Å] | 2θ [°] | Rel. Int. [%] |
|---|---|---|
| 11.40 | 7.8 | 82 |
| 10.45 | 8.5 | 38 |
| 8.16 | 10.8 | 56 |
| 7.17 | 12.3 | 51 |
| 6.83 | 13.0 | 26 |
| 5.87 | 15.1 | 42 |
| 5.72 | 15.5 | 11 |
| 5.24 | 16.9 | 57 |
| 5.02 | 17.7 | 60 |
| 4.95 | 17.9 | 19 |
| 4.45 | 19.9 | 60 |
| 4.39 | 20.2 | 19 |
| 4.22 | 21.0 | 12 |
| 4.16 | 21.4 | 100 |
| 4.05 | 22.0 | 20 |
| 4.01 | 22.2 | 37 |
| 3.95 | 22.5 | 20 |
| 3.42 | 26.1 | 31 |
| 3.34 | 26.7 | 50 |
| 3.18 | 28.0 | 9 |
| 3.16 | 28.3 | 7 |
| 3.12 | 28.6 | 37 |
| 3.09 | 28.9 | 8 |
| 3.00 | 29.8 | 7 |
| 2.96 | 30.2 | 24 |
| 2.94 | 30.4 | 10 |
| 2.87 | 31.2 | 26 |
| 2.84 | 31.5 | 7 |
| 2.82 | 31.8 | 11 |
| 2.75 | 32.6 | 19 |
| 2.62 | 34.2 | 13 |
| 2.59 | 34.7 | 13 |

Example 9. Formation of STA-18C from SAPO STA-18 Synthesized with diDABCO-C8 and Trimethylamine as SDAs A portion of the as-made material from Example 8 was calcined in dry oxygen. The material was heated at 600° C. and held at that temperature for 12 hours.

Figure 8:
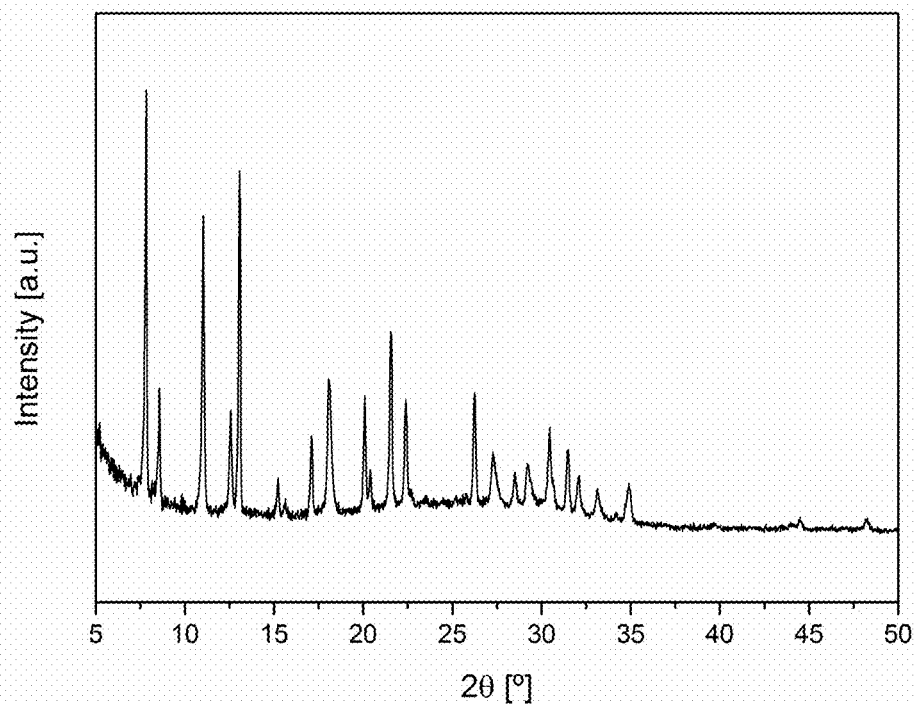
FIG. 8 is an XRD diffraction pattern of a sample of SAPO STA-18C as prepared in Example 9.

The PXRD pattern of the calcined product and the list of diffraction peaks are shown in FIG. 8 and Table 10, respectively.

TABLE 10

Diffraction peaks of calcined material of Example 9.

| d-spacing [Å] | 2θ [°] | Rel. Int. [%] |
|---|---|---|
| 11.28 | 7.8 | 96 |
| 10.31 | 8.6 | 28 |
| 8.02 | 11.0 | 74 |
| 7.04 | 12.6 | 25 |
| 6.77 | 13.1 | 100 |
| 5.82 | 15.2 | 8 |
| 5.18 | 17.1 | 20 |
| 4.91 | 18.1 | 33 |
| 4.42 | 20.1 | 28 |
| 4.35 | 20.4 | 10 |
| 4.12 | 21.6 | 44 |
| 3.97 | 22.4 | 24 |
| 3.40 | 26.2 | 27 |
| 3.27 | 27.3 | 13 |
| 3.13 | 28.5 | 8 |
| 3.06 | 29.2 | 11 |
| 2.94 | 30.5 | 21 |
| 2.84 | 31.5 | 15 |
| 2.79 | 32.1 | 10 |
| 2.70 | 33.1 | 7 |
| 2.57 | 34.9 | 9 |

Example 10. Synthesis of STA-18 Using Trimethylamine and diDABCO-C6)

A reaction gel having a molar composition:
0.3 SiO$_2$:1 Al(OH)$_3$:0.7H$_3$PO$_4$:40 H$_2$O:0.10 diDABCO-C6:0.13 trimethylamine:0.28 tetrabutylammonium hydroxide, with 2 wt. % SAPO SFW (seed)
was prepared in 125 mL pressure vessel. The reagents used and order of addition was:
  a) The required amount of phosphoric acid (H$_3$PO$_4$ 85 wt. %, Alfa Chemicals) was weighted into a 100 ml container.
  b) The required amount of Ludox PX30 (30% w/w colloidal silica; Grace Davison) and water were added to the phosphoric acid and stirred.
  c) The required amount of aluminium hydroxide (Al(OH)$_3$, Sigma Aldrich) was added to the above mixture.
  d) After stirring for 30 minutes, diDABCO-C6 (Alfa Aesar) was added.
  e) Trimethylamine (45 wt. %, Sigma Aldrich) was added over the above solution and the mixture was stirred for 10 minutes.
  f) Tetrabutylammonium hydroxide (40 wt. %, Sigma Aldrich) was finally added to the mixture.
  g) 2 wt. % of SAPO SFW seeds were finally added.

The final gel was stirred continuously at room temperature for at least 2 hours during the preparation procedure, until homogeneous, prior to being transferred to a Teflon-lined stainless steel autoclave and heated in a rotating oven (30 rpm) at 190° C. for 4 days. The contents of the bomb were centrifuged and washed with de-mineralised water. The resulting product was dried overnight at 110° C.

Figure 9:
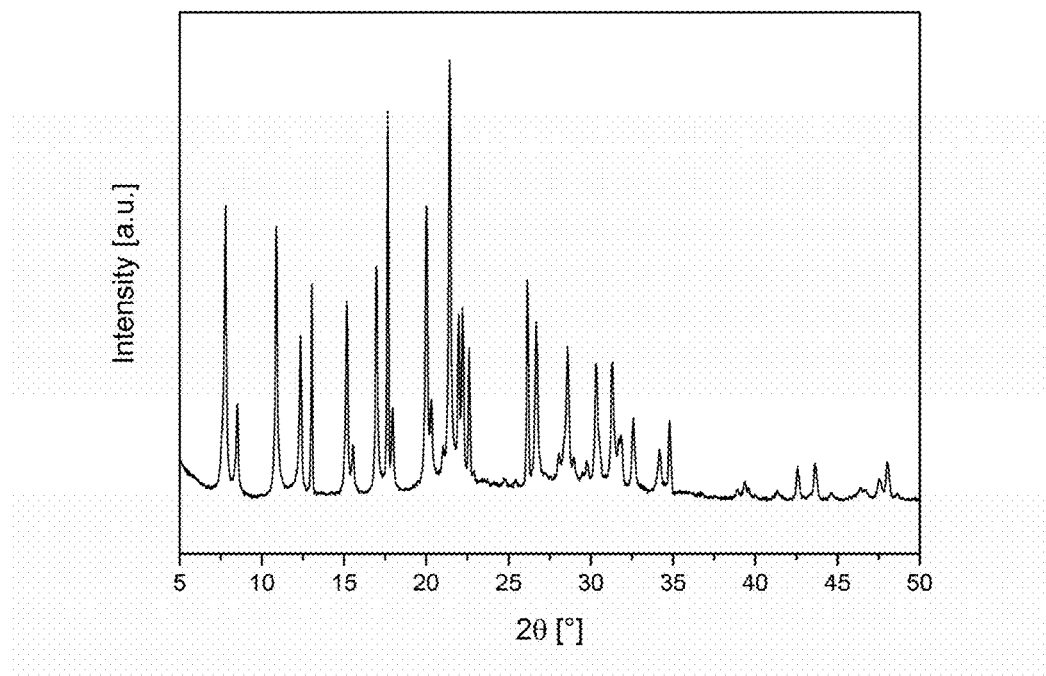
FIG. 9 is an XRD diffraction pattern of a sample of SAPO STA-18AP as prepared in Example 10.

The powder XRD pattern is shown in FIG. 9 and comprises the diffraction peaks in Table 11. Analysis by powder XRD indicated that the product was phase pure SFW.

TABLE 11

Diffraction peaks of as prepared material of Example 10.

| d-spacing [Å] | 2θ [°] | Rel. Int. [%] |
|---|---|---|
| 11.37 | 7.8 | 61 |
| 10.40 | 8.5 | 20 |
| 8.13 | 10.9 | 63 |
| 7.20 | 12.3 | 37 |
| 6.73 | 13.0 | 47 |
| 5.84 | 15.2 | 45 |
| 5.70 | 15.5 | 11 |
| 5.22 | 17.0 | 52 |
| 5.01 | 17.7 | 89 |
| 4.94 | 17.9 | 18 |
| 4.43 | 20.0 | 66 |
| 4.38 | 20.3 | 18 |
| 4.21 | 21.1 | 8 |
| 4.14 | 21.4 | 100 |
| 4.03 | 22.0 | 33 |
| 4.00 | 22.2 | 37 |
| 3.93 | 22.6 | 32 |
| 3.40 | 26.2 | 48 |
| 3.34 | 26.7 | 38 |
| 3.17 | 28.1 | 6 |
| 3.16 | 28.2 | 7 |
| 3.12 | 28.6 | 32 |
| 3.08 | 28.9 | 5 |
| 3.02 | 29.5 | 6 |
| 2.95 | 30.3 | 27 |
| 2.93 | 30.5 | 10 |
| 2.85 | 31.3 | 28 |
| 2.83 | 31.6 | 8 |
| 2.81 | 31.7 | 10 |
| 2.76 | 32.6 | 17 |
| 2.62 | 34.2 | 10 |
| 2.58 | 34.8 | 17 |

Example 11. Formation of STA-18C

The as-made material of Example 6 was activated by calcination in air. The material was heated to 110° C. at 2° C. min$^{-1}$ and held at 110° C. for 10 hours, then heated to 450° C. at 5° C./min$^{-1}$ and held at 450° C. for 16 hours. The material was then heated to 550° C. at 5° C. min$^{-1}$ at held at 550° C. for 16 hours.

Figure 10:
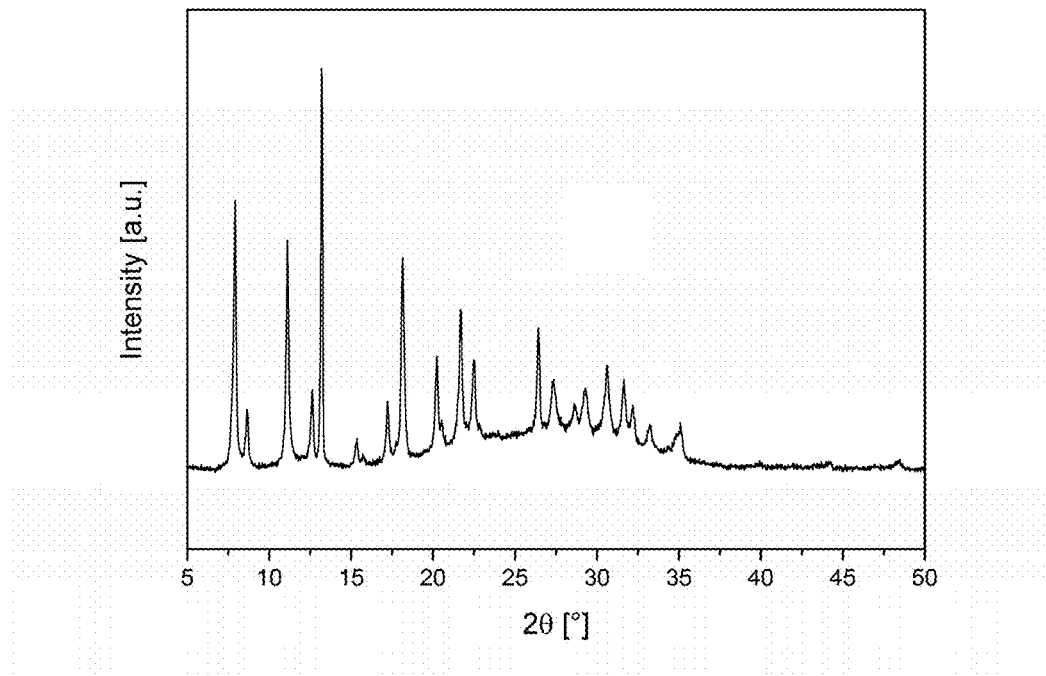
FIG. 10 is an XRD diffraction pattern of a sample of SAPO STA-18C as prepared in Example 11.

The PXRD pattern of the calcined product and the list of diffraction peaks are shown in FIG. 10 and Table 12, respectively.

TABLE 12

Diffraction peaks of calcined material of Example 5.

| d-spacing [Å] | 2θ [°] | Rel. Int. [%] |
|---|---|---|
| 11.19 | 7.9 | 62 |
| 10.23 | 8.6 | 14 |
| 7.96 | 11.1 | 57 |
| 7.01 | 12.6 | 19 |
| 6.70 | 13.2 | 100 |
| 5.77 | 15.3 | 6 |
| 5.14 | 17.2 | 15 |
| 4.88 | 18.1 | 51 |
| 4.38 | 20.2 | 23 |
| 4.33 | 20.5 | 6 |

TABLE 12-continued

Diffraction peaks of calcined material of Example 5.

| d-spacing [Å] | 2θ [°] | Rel. Int. [%] |
|---|---|---|
| 4.09 | 21.7 | 34 |
| 3.95 | 22.5 | 21 |
| 3.37 | 26.4 | 27 |
| 3.26 | 27.3 | 14 |
| 3.11 | 28.7 | 7 |
| 3.05 | 29.3 | 12 |
| 2.92 | 30.6 | 19 |
| 2.83 | 31.6 | 15 |
| 2.78 | 32.2 | 9 |
| 2.70 | 33.2 | 6 |
| 2.57 | 34.9 | 6 |

What is claimed is:

1. A molecular sieve (STA-18) comprising an SFW type framework with phosphate within the framework.

2. The molecular sieve of claim 1, wherein the molecular sieve is a silicoaluminophosphate (SAPO), a metal silicoaluminophosphate (MeSAPO) or a metal aluminophosphate (MeAPO).

3. The molecular sieve of claim 1, where the SFW structure is free from structural faulting.

4. The molecular sieve of claim 1, where the molecular sieve comprises at least one metal within the framework where the metal is selected from at least one of the metals of Groups of the Periodic Table IIIA, IB, IIB, VA, VIA, VIIA, VIIIA and combinations thereof.

5. The molecular sieve of claim 1, where the molecular sieve further comprises at least one extra-framework transition metal selected from the group consisting of Ag, Au, Ce, Co, Cr, Cu, Fe, Ga, In, Ir, Mn, Mo, Nb, Ni, Pd, Pt, Re, Rh, Ru, Sn, Ta, V, W and Zn.

6. The molecular sieve of claim 1, where the molecular sieve is calcined or contains one of more structure directing agents (SDAs).

7. The molecular sieve of claim 1, where the molecular sieve is a silicoaluminophosphate.

8. The molecular sieve of claim 7 having the molar relationship: $(Si_xAl_yP_z)O_2$, where x is the mole fraction of Si and has a value from 0.05 to 0.3, y is the mole fraction of Al and has a value from 0.4 to 0.6, z is the mole fraction of P and has a value from 0.2 to 0.45, and x+y+z=1.

9. The molecular sieve of claim 8, where the molecular sieve is a calcined molecular sieve and has at least one property selected from the group consisting of: a characteristic X-ray powder diffraction pattern substantially similar to that shown in FIG. 4; and a characteristic X-ray powder diffraction pattern comprising 2-theta positions at 7.8 (vs), 11.0 (vs), 13.0 (vs) and 21.5 (s)±0.2 with the corresponding relative intensity shown in parenthesis, where the corresponding relative intensities are w (weak)<20; m (medium) is ≥20 and <40; s (strong) is ≥40 and <60; and vs (very strong) is ≥60.

10. The molecular sieve of claim 8, where the molecular sieve further comprises one or more structure directing agents (SDAs).

11. The molecular sieve of claim 10, where the structure directing agents comprises a lower alkyl amine and a 1,4-diazabicyclo[2.2.2]octane derivative.

12. The molecular sieve of claim 11, where the lower alkyl amine is trimethylamine or N,N-dimethylethylamine.

13. The molecular sieve of claim 11, where the 1,4-diazabicyclo[2.2.2]octane derivative is a 1,6-(1,4-diazabicyclo[2.2.2]octane)hexyl cation, or 1,7-(1,4-diazabicyclo [2.2.2]octane)heptyl cation or a 1,8-(1,4-diazabicyclo[2.2.2]octane)octyl cation.

14. The molecular sieve of claim 13, where the lower alkyl amine is trimethylamine or N,N-dimethylethylamine and the 1,4-diazabicyclo[2.2.2]octane derivative is a 1,7-(1, 4-diazabicyclo[2.2.2]octane)heptyl cation, where the molecular sieve has at least one property selected from the group consisting of: a characteristic X-ray powder diffraction pattern substantially similar to that shown in FIG. 5; and a characteristic X-ray powder diffraction pattern comprising 2-theta positions at 7.7 (vs), 10.8 (s-vs), 12.3 (m-s), 16.9 (s), 17.6 (s), 19.9 (s-vs), 21.3 (vs) and 26.7 (m-s)±0.2 with the corresponding relative intensity shown in parenthesis, where the corresponding relative intensities are w (weak)<20; m (medium) is ≥20 and <40; s (strong) is ≥40 and <60; and vs (very strong) is ≥60.

15. The molecular sieve of claim 13, where the lower alkyl amine is trimethylamine or N,N-dimethylethylamine and the 1,4-diazabicyclo[2.2.2]octane derivative is a 1,8-(1, 4-diazabicyclo[2.2.2]octane)octyl cation, where the molecular sieve has at least one property selected from the group consisting of: a characteristic X-ray powder diffraction pattern substantially similar to that shown in FIG. 7; and a characteristic X-ray powder diffraction pattern comprising 2-theta positions at 7.8 (vs), 10.8 (s), 12.3 (s), 16.9 (s), 17.7 (s-vs), 19.9 (v-vs), 21.4 (vs) and 26.7 (s)±0.2 with the corresponding relative intensity shown in parenthesis, where the corresponding relative intensities are w (weak)<20; m (medium) is ≥20 and <40; s (strong) is ≥40 and <60; and vs (very strong) is ≥60.

16. The molecular sieve of claim 11, where the lower alkyl amine is trimethylamine or N,N-dimethylethylamine and the 1,4-diazabicyclo[2.2.2]octane derivative is a 1,6-(1, 4-diazabicyclo[2.2.2]octane)hexyl cation, where the molecular sieve has at least one property selected from the group consisting of: a characteristic X-ray powder diffraction pattern substantially similar to that shown in FIG. 1; and a characteristic X-ray powder diffraction pattern comprising 2-theta positions at 7.7 (vs), 10.8 (vs), 12.3 (m-s), 16.9 (s), 17.6 (s), 19.9 (s-vs), 21.3 (vs) and 26.6 (s)±0.2 with the corresponding relative intensity shown in parenthesis, where the corresponding relative intensities are w (weak)<20; m (medium) is ≥20 and <40; s (strong) is ≥40 and <60; and vs (very strong) is ≥60.

17. A catalyst comprising a molecular sieve of claim 1.

18. A catalyst article for treating exhaust gas comprising a catalyst composition of claim 17, where the catalyst is disposed on and/or within a honeycomb structure.

19. A method for synthesizing a molecular sieve of claim 1, the method comprising:
   a. forming heating a reaction mixture comprising: (a) at least one source of alumina, (b) at least one source of silica, (c) at least one source of phosphorus, and (d) one or more structure directing agents (SDAs);
   b. forming molecular sieve crystals having a SFW framework and the structure directing agent, and
   c. recovering at least a portion of the molecular sieve crystals from the reaction mixture,
   wherein the reaction mixture is a gel having a molar compositional ratio of:

| | |
|---|---|
| P/A | 0.5-0.99 |
| $MeO_2$/A | 0.02-1.0 |
| SDA1 (1,4-diazabicyclo[2.2.2]octane derivative)/A | 0.1-06 |
| SDA2 (lower alkyl amine)/A | 0.1-0.6 |
| Lower alkyl ammonia hydroxide/A | 0.1-0.6 |
| $H_2O$/A | 20-200 | where P the source of phosphorous and is calculated as being in the oxide form ($P_2O_5$), A is Al, Fe, Cr, B, Ga or combinations thereof and is calculated as being in the oxide form ($A_2O_3$); and Me is Si, Ge, Mg or combinations thereof and is calculated as being in the oxide form ($MO_2$).

20. A method for treating an exhaust gas comprising contacting a combustion exhaust gas containing $NO_x$ and/or $NH_3$ with a catalyst according to claim 1 to selectively reduce at least a portion of the $NO_x$ into $N_2$ and $H_2O$ and/or oxidize at least a portion of the $NH_3$.

21. A method for treating an exhaust gas comprising contacting a combustion exhaust gas containing $NO_x$ with a passive NOx absorber comprising a molecular sieve of claim 1.

22. A composition comprising: (a) at least one source of alumina, (b) at least one source of silica; (c) a lower alkyl amine, (d) a 1,4-diazabicyclo [2.2.2] octane derivative comprising a 1,6-(1,4-diazabicyclo[2.2.2]octane)hexyl cation, a 1,7-(1,4-diazabicyclo [2.2.2]octane) heptyl cation or a 1,8-(1,4-diazabicyclo[2.2.2]octane)octyl cation, and (e) a lower alkyl ammonium hydroxide, wherein the composition has a molar compositional ratio of:

| | |
|---|---|
| P/A | 0.5-0.99 |
| $MeO_2$/A | 0.02-1.0 |
| SDA1 (1,4-diazabicyclo[2.2.2]octane derivative)/A | 0.1-0.6 |
| SDA2 (lower alkyl amine)/A | 0.1-0.6 |
| Lower alkyl ammonia hydroxide/A | 0.1-0.6 |
| $H_2O$/A | 20-200 | where P the source of phosphorous and is calculated as being in the oxide form ($P_2O_5$), A is Al, Fe, Cr, B, Ga or combinations thereof and is calculated as being in the oxide form ($A_2O_3$); and Me is Si, Ge, Mg or combinations thereof and is calculated as being in the oxide form ($MO_2$).

* * * * *